(12) United States Patent
Wheeler et al.

(10) Patent No.: US 12,396,729 B2
(45) Date of Patent: Aug. 26, 2025

(54) FASTENER APPLICATOR WITH INTERLOCK

(71) Applicant: DATASCOPE CORP., Wayne, NJ (US)

(72) Inventors: William K. Wheeler, Berthoud, CO (US); Ashik A. Mohan, Petaluma, CA (US)

(73) Assignee: DATASCOPE CORPORATION, Wayne, NJ (US)

( * ) Notice: Subject to any disclaimer, the term of this patent is extended or adjusted under 35 U.S.C. 154(b) by 0 days.

(21) Appl. No.: 18/158,866

(22) Filed: Jan. 24, 2023

(65) Prior Publication Data

US 2023/0157692 A1 May 25, 2023

Related U.S. Application Data

(60) Continuation of application No. 16/599,779, filed on Oct. 11, 2019, now Pat. No. 11,564,689, which is a
(Continued)

(51) Int. Cl.
*A61B 17/10* (2006.01)
*A61B 17/064* (2006.01)
(Continued)

(52) U.S. Cl.
CPC .......... *A61B 17/10* (2013.01); *A61B 17/0643* (2013.01); *A61B 17/072* (2013.01);
(Continued)

(58) Field of Classification Search
CPC .... A61B 2017/2925; A61B 2017/2913; A61B 2017/2919; A61B 2017/2924;
(Continued)

(56) References Cited

U.S. PATENT DOCUMENTS

| 729,116 A | 5/1903 | Barnstead |
| 1,756,670 A | 4/1930 | Treat |

(Continued)

FOREIGN PATENT DOCUMENTS

| CN | 1864642 A | 11/2006 |
| CN | 1883411 A | 12/2006 |

(Continued)

OTHER PUBLICATIONS

International Search Report and Written Opinion of PCT Application No. PCT/US07/068147, dated Sep. 17, 2008, 6 pages total.
(Continued)

*Primary Examiner* — Majid Jamialahmadi

(57) ABSTRACT

The present disclosure relates to a fastener applicator including a handle, a first trigger coupled rotatably with respect to the handle, and a second trigger coupled rotatably with respect to the handle. An interlock is disposed with the second trigger and comprises a cam follower engaged in a cam channel that selectively prevents rotation of the second trigger relative to the first trigger depending on a location of the cam follower within the cam channel. The location of the cam follower in the cam channel is set by a position of the first trigger. Methods of operating the various embodiments disclosed are also provided.

6 Claims, 14 Drawing Sheets

Related U.S. Application Data division of application No. 15/037,963, filed as application No. PCT/US2014/066438 on Nov. 19, 2014, now Pat. No. 10,485,545.

(60) Provisional application No. 61/906,290, filed on Nov. 19, 2013.

(51) Int. Cl.

| | | |
|---|---|---|
| *A61B 17/072* | (2006.01) | |
| *A61B 17/08* | (2006.01) | |
| *A61B 17/122* | (2006.01) | |
| *A61B 17/128* | (2006.01) | |
| *A61B 17/00* | (2006.01) | |

(52) U.S. Cl.
CPC .......... *A61B 17/083* (2013.01); *A61B 17/122* (2013.01); *A61B 17/1285* (2013.01); *A61B 2017/00243* (2013.01)

(58) Field of Classification Search
CPC .... A61B 2017/2912; A61B 2017/2922; A61B 17/2909; A61B 17/0643; A61B 17/072; A61B 17/10; A61B 17/083; A61B 17/122; A61B 17/068; A61B 17/07207; A61B 17/29

See application file for complete search history.

(56) References Cited

U.S. PATENT DOCUMENTS

| | | |
|---|---|---|
| 2,659,371 A | 11/1953 | Schnee |
| 3,139,563 A | 6/1964 | Freeman |
| 3,336,133 A | 8/1967 | Funatsu |
| 3,361,133 A | 1/1968 | Kimberley |
| 3,525,340 A | 8/1970 | Gilbert |
| 3,746,002 A | 7/1973 | Haller |
| 3,993,076 A | 11/1976 | Fogarty |
| 4,016,883 A | 4/1977 | Wright, Jr. |
| 4,060,089 A | 11/1977 | Noiles |
| 4,241,861 A | 12/1980 | Fleischer |
| 4,257,419 A | 3/1981 | Ewald |
| 4,271,828 A | 6/1981 | Angelchik |
| 4,390,019 A | 6/1983 | Leveen |
| 4,402,445 A | 9/1983 | Green |
| 4,414,721 A | 11/1983 | Hufnagel |
| 4,487,205 A | 12/1984 | Di Giovanni |
| 4,489,725 A | 12/1984 | Casey |
| 4,506,670 A | 3/1985 | Crossley |
| 4,506,671 A | 3/1985 | Green |
| 4,548,201 A | 10/1985 | Yoon |
| 4,610,250 A | 9/1986 | Green |
| 4,702,247 A | 10/1987 | Blake, III |
| 4,724,839 A | 2/1988 | Bedi |
| 4,754,758 A | 7/1988 | Li |
| 4,805,617 A | 2/1989 | Bedi |
| 4,822,348 A | 4/1989 | Casey |
| 4,924,864 A | 5/1990 | Danzig |
| 4,960,420 A | 10/1990 | Goble |
| 4,976,722 A | 12/1990 | Failla |
| 4,988,355 A | 1/1991 | Leveen |
| 5,002,552 A | 3/1991 | Casey |
| 5,062,846 A | 11/1991 | Oh |
| 5,094,753 A | 3/1992 | Allington |
| 5,127,915 A | 7/1992 | Mattson |
| 5,132,014 A | 7/1992 | Allington |
| 5,156,315 A | 10/1992 | Green |
| 5,156,614 A | 10/1992 | Green |
| 5,160,339 A | 11/1992 | Chen |
| 5,160,624 A | 11/1992 | Clay |
| 5,171,247 A | 12/1992 | Hughett |
| 5,171,249 A | 12/1992 | Stefanchik |
| 5,171,253 A | 12/1992 | Klieman |
| 5,173,188 A | 12/1992 | Winter |
| 5,193,554 A | 3/1993 | McQuilkin |
| 5,198,197 A | 3/1993 | Clay |
| 5,207,691 A | 5/1993 | Nardella |
| 5,246,456 A | 9/1993 | Wilkinson |
| 5,250,195 A | 10/1993 | Winter |
| 5,253,793 A | 10/1993 | Green |
| 5,257,999 A | 11/1993 | Slanetz, Jr. |
| 5,268,102 A | 12/1993 | Clay |
| 5,268,103 A | 12/1993 | Jameson |
| 5,269,930 A | 12/1993 | Jameson |
| 5,282,812 A | 2/1994 | Suarez, Jr. |
| 5,284,488 A | 2/1994 | Sideris |
| 5,296,145 A | 3/1994 | Allington |
| 5,306,234 A | 4/1994 | Johnson |
| 5,314,424 A | 5/1994 | Nicholas |
| 5,336,232 A | 8/1994 | Green |
| 5,352,238 A | 10/1994 | Green |
| 5,358,506 A | 10/1994 | Green |
| 5,358,510 A | 10/1994 | Luscombe |
| 5,366,458 A | 11/1994 | Korthoff |
| 5,366,459 A | 11/1994 | Yoon |
| 5,368,600 A | 11/1994 | Failla |
| 5,379,933 A | 1/1995 | Green |
| 5,413,268 A | 5/1995 | Green |
| 5,423,471 A | 6/1995 | Mastri |
| 5,425,705 A | 6/1995 | Evard |
| 5,425,740 A | 6/1995 | Hutchinson, Jr. |
| 5,441,507 A | 8/1995 | Wilk |
| 5,462,215 A | 10/1995 | Mola |
| 5,462,558 A | 10/1995 | Kolesa |
| 5,465,895 A | 11/1995 | Knodel |
| 5,470,006 A | 11/1995 | Rodak |
| 5,470,009 A | 11/1995 | Rodak |
| 5,474,567 A | 12/1995 | Stefanchik |
| 5,485,947 A | 1/1996 | Olson |
| 5,490,856 A | 2/1996 | Person |
| 5,501,693 A | 3/1996 | Gravener |
| 5,507,797 A | 4/1996 | Suzuki |
| 5,509,920 A | 4/1996 | Phillips |
| 5,531,744 A | 7/1996 | Nardella |
| 5,536,251 A | 7/1996 | Evard |
| 5,547,117 A | 8/1996 | Hamblin |
| 5,549,621 A | 8/1996 | Bessler |
| 5,551,622 A | 9/1996 | Yoon |
| 5,554,169 A | 9/1996 | Green |
| 5,560,530 A | 10/1996 | Bolanos |
| 5,569,272 A | 10/1996 | Reed |
| 5,573,169 A | 11/1996 | Green |
| 5,575,802 A | 11/1996 | McQuilkin |
| 5,580,067 A | 12/1996 | Hamblin |
| 5,584,989 A | 12/1996 | Jameson |
| 5,591,178 A | 1/1997 | Green |
| 5,597,107 A | 1/1997 | Knodel |
| 5,601,573 A | 2/1997 | Fogelberg |
| 5,601,707 A | 2/1997 | Clay |
| 5,605,272 A | 2/1997 | Witt |
| 5,605,273 A | 2/1997 | Hamblin |
| 5,614,089 A | 3/1997 | Allington |
| 5,620,452 A | 4/1997 | Yoon |
| 5,624,453 A | 4/1997 | Ahmed |
| 5,626,592 A | 5/1997 | Phillips |
| 5,632,432 A | 5/1997 | Schulze |
| 5,635,070 A | 6/1997 | Allington |
| 5,643,291 A | 7/1997 | Pier |
| 5,643,319 A | 7/1997 | Green |
| 5,645,553 A | 7/1997 | Kolesa |
| 5,653,373 A | 8/1997 | Green |
| 5,653,885 A | 8/1997 | Jameson |
| 5,655,698 A | 8/1997 | Yoon |
| 5,658,300 A | 8/1997 | Bito |
| 5,662,259 A | 9/1997 | Yoon |
| 5,662,260 A | 9/1997 | Yoon |
| 5,665,085 A | 9/1997 | Nardella |
| 5,669,544 A | 9/1997 | Schulze |
| 5,676,676 A | 10/1997 | Porter |
| 5,690,828 A | 11/1997 | Clay |
| 5,695,502 A | 12/1997 | Pier |
| 5,697,938 A | 12/1997 | Jensen |
| 5,706,998 A | 1/1998 | Plyley |

(56) References Cited

U.S. PATENT DOCUMENTS

| | | |
|---|---|---|
| 5,713,896 A | 2/1998 | Nardella |
| 5,713,912 A | 2/1998 | Porter |
| 5,715,987 A | 2/1998 | Kelley |
| 5,720,756 A | 2/1998 | Green |
| 5,722,982 A | 3/1998 | Ferreira |
| 5,725,537 A | 3/1998 | Green |
| 5,725,538 A | 3/1998 | Green |
| 5,728,110 A | 3/1998 | Mdal |
| 5,735,874 A | 4/1998 | Measamer |
| 5,738,498 A | 4/1998 | Allington |
| 5,741,283 A | 4/1998 | Fahy |
| 5,749,893 A | 5/1998 | Vidal |
| 5,750,027 A | 5/1998 | Allington |
| 5,755,559 A | 5/1998 | Allington |
| 5,755,726 A | 5/1998 | Pratt |
| 5,759,193 A | 6/1998 | Burbank |
| 5,772,673 A | 6/1998 | Cuny |
| 5,779,718 A | 7/1998 | Green |
| 5,794,834 A | 8/1998 | Hamblin |
| 5,797,932 A | 8/1998 | Min |
| 5,833,695 A | 11/1998 | Yoon |
| 5,833,698 A | 11/1998 | Hinchliffe |
| 5,833,700 A | 11/1998 | Fogelberg |
| 5,843,101 A | 12/1998 | Fry |
| 5,846,255 A | 12/1998 | Casey |
| 5,849,019 A | 12/1998 | Yoon |
| 5,855,311 A | 1/1999 | Hamblin |
| 5,865,791 A | 2/1999 | Whayne |
| 5,868,761 A | 2/1999 | Nicholas |
| 5,868,784 A | 2/1999 | Riza |
| 5,893,879 A | 4/1999 | Hirshowitz |
| 5,911,881 A | 6/1999 | Clay |
| 5,915,615 A | 6/1999 | Bauer |
| 5,921,997 A | 7/1999 | Fogelberg |
| 5,932,095 A | 8/1999 | Walters |
| 5,964,774 A | 10/1999 | McKean |
| 5,972,022 A | 10/1999 | Huxel |
| 5,976,159 A | 11/1999 | Bolduc |
| 6,015,417 A | 1/2000 | Reynolds, Jr. |
| 6,036,706 A | 3/2000 | Morejohn |
| 6,042,599 A | 3/2000 | Huttner |
| 6,051,003 A | 4/2000 | Chu |
| 6,071,408 A | 6/2000 | Allington |
| 6,083,399 A | 7/2000 | Jameson |
| 6,086,767 A | 7/2000 | Walters |
| 6,139,555 A | 10/2000 | Hart |
| 6,139,563 A | 10/2000 | Cosgrove, III |
| 6,149,814 A | 11/2000 | Allington |
| 6,152,144 A | 11/2000 | Lesh |
| 6,162,239 A | 12/2000 | Manhes |
| 6,206,897 B1 | 3/2001 | Jamiolkowski |
| 6,231,561 B1 | 5/2001 | Frazier |
| 6,238,414 B1 | 5/2001 | Griffiths |
| 6,241,890 B1 | 6/2001 | Clay |
| 6,251,267 B1 | 6/2001 | Allington |
| 6,273,897 B1 | 8/2001 | Dalessandro |
| 6,280,407 B1 | 8/2001 | Manna |
| 6,290,674 B1 | 9/2001 | Roue |
| 6,294,088 B1 | 9/2001 | Allington |
| 6,296,769 B1 | 10/2001 | Walters |
| 6,319,410 B1 | 11/2001 | Allington |
| 6,325,810 B1 | 12/2001 | Hamilton |
| 6,328,727 B1 | 12/2001 | Frazier |
| 6,332,864 B1 | 12/2001 | Schweich, Jr. |
| 6,338,710 B1 | 1/2002 | Takahashi |
| 6,379,366 B1 | 4/2002 | Fleischman |
| 6,387,106 B1 | 5/2002 | Howell |
| 6,391,038 B2 | 5/2002 | Vargas |
| 6,406,485 B1 | 6/2002 | Hossain |
| 6,419,669 B1 | 7/2002 | Frazier |
| 6,419,682 B1 | 7/2002 | Appleby |
| 6,421,920 B1 | 7/2002 | Jensen |
| RE37,814 E | 8/2002 | Allgeyer |
| 6,436,097 B1 | 8/2002 | Nardella |
| 6,436,108 B1 | 8/2002 | Mears |
| 6,458,100 B2 | 10/2002 | Roue |
| 6,461,363 B1 | 10/2002 | Gadberry |
| 6,461,368 B2 | 10/2002 | Fogarty |
| 6,478,804 B2 | 11/2002 | Vargas |
| 6,488,689 B1 | 12/2002 | Kaplan |
| 6,503,259 B2 | 1/2003 | Huxel |
| 6,508,829 B1 | 1/2003 | Levinson |
| 6,517,556 B1 | 2/2003 | Monassevitch |
| 6,520,972 B2 | 2/2003 | Peters |
| 6,527,786 B1 | 3/2003 | Davis |
| 6,551,303 B1 | 4/2003 | Van Tassel |
| 6,558,408 B1 | 5/2003 | Fogarty |
| 6,561,969 B2 | 5/2003 | Frazier |
| 6,579,304 B1 | 6/2003 | Hart |
| 6,582,451 B1 | 6/2003 | Marucci |
| 6,592,600 B1 | 7/2003 | Nicolo |
| 6,629,988 B2 | 10/2003 | Weadock |
| 6,638,282 B2 | 10/2003 | Ramsey |
| 6,641,557 B1 | 11/2003 | Frazier |
| 6,644,618 B1 | 11/2003 | Balbo |
| 6,652,555 B1 | 11/2003 | Vantassel |
| 6,652,556 B1 | 11/2003 | Vantassel |
| 6,656,205 B1 | 12/2003 | Manhes |
| 6,663,653 B2 | 12/2003 | Akerfeldt |
| 6,685,715 B2 | 2/2004 | Danitz |
| 6,689,150 B1 | 2/2004 | Vantassel |
| 6,692,507 B2 | 2/2004 | Pugsley |
| 6,699,258 B1 | 3/2004 | Sadler |
| 6,702,825 B2 | 3/2004 | Frazier |
| 6,702,826 B2 | 3/2004 | Liddicoat |
| 6,712,804 B2 | 3/2004 | Roue |
| 6,716,232 B1 | 4/2004 | Vidal |
| 6,723,109 B2 | 4/2004 | Solingen |
| 6,730,108 B2 | 5/2004 | Van Tassel |
| 6,746,461 B2 | 6/2004 | Fry |
| 6,746,472 B2 | 6/2004 | Frazier |
| 6,755,338 B2 | 6/2004 | Hahnen |
| 6,776,783 B1 | 8/2004 | Frantzen |
| 6,776,785 B1 | 8/2004 | Yencho |
| 6,780,195 B2 | 8/2004 | Porat |
| 6,790,172 B2 | 9/2004 | Alferness |
| 6,817,972 B2 | 11/2004 | Snow |
| 6,821,285 B2 | 11/2004 | Laufer |
| 6,830,174 B2 | 12/2004 | Hillstead |
| 6,840,246 B2 | 1/2005 | Downing |
| 6,863,675 B2 | 3/2005 | Wilson, Jr. |
| 6,893,391 B2 | 5/2005 | Taylor |
| 6,916,332 B2 | 7/2005 | Adams |
| 6,926,712 B2 | 8/2005 | Phan |
| 6,949,113 B2 | 9/2005 | Van Tassel |
| 6,974,462 B2 | 12/2005 | Sater |
| 6,994,092 B2 | 2/2006 | van der Burg |
| 7,001,412 B2 | 2/2006 | Gallagher |
| 7,033,378 B2 | 4/2006 | Smith |
| 7,044,134 B2 | 5/2006 | Khairkhahan |
| 7,070,083 B2 | 7/2006 | Jankowski |
| 7,077,856 B2 | 7/2006 | Whitman |
| 7,083,636 B2 | 8/2006 | Kortenbach |
| 7,108,703 B2 | 9/2006 | Danitz |
| 7,128,073 B1 | 10/2006 | Van Der Burg |
| 7,152,605 B2 | 12/2006 | Khairkhahan |
| 7,220,272 B2 | 5/2007 | Weadock |
| 7,226,458 B2 | 6/2007 | Kaplan |
| 7,285,131 B1 | 10/2007 | Bombard |
| 7,300,444 B1 | 11/2007 | Nielsen |
| 7,316,696 B2 | 1/2008 | Wilson, Jr. |
| 7,326,223 B2 | 2/2008 | Wilson, Jr. |
| 7,407,076 B2 | 8/2008 | Racenet |
| 7,422,783 B2 | 9/2008 | Tremblay |
| 7,427,279 B2 | 9/2008 | Frazier |
| 7,438,208 B2 | 10/2008 | Larson |
| 7,438,718 B2 | 10/2008 | Milliman |
| 7,473,258 B2 | 1/2009 | Clauson |
| 7,473,261 B2 | 1/2009 | Rennich |
| 7,497,865 B2 | 3/2009 | Willis |
| 7,503,474 B2 | 3/2009 | Hillstead |
| 7,527,634 B2 | 5/2009 | Zenati |
| 7,543,730 B1 | 6/2009 | Marczyk |
| 7,547,315 B2 | 6/2009 | Peterson |

(56) References Cited

U.S. PATENT DOCUMENTS

| | | |
|---|---|---|
| 7,549,983 B2 | 6/2009 | Roue |
| 7,553,315 B2 | 6/2009 | Kortenbach |
| 7,556,185 B2 | 7/2009 | Viola |
| 7,563,267 B2 | 7/2009 | Goldfarb |
| 7,566,336 B2 | 7/2009 | Corcoran |
| 7,569,064 B1 | 8/2009 | Hausen |
| 7,597,704 B2 | 10/2009 | Frazier |
| 7,628,797 B2 | 12/2009 | Tai |
| 7,635,073 B2 | 12/2009 | Heinrich |
| 7,645,285 B2 | 1/2010 | Cosgrove |
| 7,648,514 B1 | 1/2010 | Nakao |
| 7,658,311 B2 | 2/2010 | Boudreaux |
| 7,658,312 B2 | 2/2010 | Vidal |
| 7,665,646 B2 | 2/2010 | Prommersberger |
| 7,673,782 B2 | 3/2010 | Hess |
| 7,681,772 B2 | 3/2010 | Green |
| 7,686,200 B2 | 3/2010 | Peterson |
| 7,686,759 B2 | 3/2010 | Sater |
| 7,686,820 B2 | 3/2010 | Huitema |
| 7,699,860 B2 | 4/2010 | Huitema |
| 7,713,276 B2 | 5/2010 | Dennis |
| 7,717,312 B2 | 5/2010 | Beetel |
| 7,717,937 B2 | 5/2010 | Wahr |
| 7,722,527 B2 | 5/2010 | Bouchier |
| 7,722,628 B2 | 5/2010 | Stokes |
| 7,722,641 B2 | 5/2010 | Van Der Burg |
| 7,722,643 B2 | 5/2010 | Schaller |
| 7,727,142 B2 | 6/2010 | Hjelle |
| 7,727,189 B2 | 6/2010 | Vantassel |
| 7,731,073 B2 | 6/2010 | Wixey |
| 7,735,493 B2 | 6/2010 | van der Burg |
| 7,735,703 B2 | 6/2010 | Morgan |
| 7,740,159 B2 | 6/2010 | Shelton, IV |
| 7,749,249 B2 | 7/2010 | Gelbart |
| 7,753,245 B2 | 7/2010 | Boudreaux |
| 7,753,248 B2 | 7/2010 | Viola |
| 7,757,924 B2 | 7/2010 | Gerbi |
| 7,758,610 B2 | 7/2010 | Kanner |
| 7,766,207 B2 | 8/2010 | Mather |
| 7,766,924 B1 | 8/2010 | Bombard |
| 7,770,774 B2 | 8/2010 | Mastri |
| 7,780,683 B2 | 8/2010 | Roue |
| 7,780,685 B2 | 8/2010 | Hunt |
| 7,794,475 B2 | 9/2010 | Hess |
| 7,819,886 B2 | 10/2010 | Whitfield |
| 7,828,188 B2 | 11/2010 | Jankowski |
| 7,828,810 B2 | 11/2010 | Liddicoat |
| 7,845,533 B2 | 12/2010 | Marczyk |
| 7,845,588 B1 | 12/2010 | Goodick |
| 7,846,168 B2 | 12/2010 | Liddicoat |
| 7,862,571 B2 | 1/2011 | Dennis |
| 7,866,523 B1 | 1/2011 | White |
| 7,891,534 B2 | 2/2011 | Wenchell |
| 7,892,244 B2 | 2/2011 | Monassevitch |
| 7,896,895 B2 | 3/2011 | Boudreaux |
| 7,896,896 B2 | 3/2011 | Viola |
| 7,909,224 B2 | 3/2011 | Prommersberger |
| 7,913,893 B2 | 3/2011 | Mastri |
| 7,926,691 B2 | 4/2011 | Viola |
| 7,931,578 B2 | 4/2011 | Whayne |
| 7,950,561 B2 | 5/2011 | Aranyi |
| 7,951,069 B2 | 5/2011 | Bertolero |
| 7,951,147 B2 | 5/2011 | Privitera |
| 7,954,686 B2 | 6/2011 | Baxter, III |
| 7,959,051 B2 | 6/2011 | Smith |
| 7,959,555 B2 | 6/2011 | Dietz |
| 7,967,178 B2 | 6/2011 | Scirica |
| 7,967,180 B2 | 6/2011 | Scirica |
| 7,992,757 B2 | 8/2011 | Wheeler |
| 8,002,795 B2 | 8/2011 | Beetel |
| 8,007,504 B2 | 8/2011 | Zenati |
| 8,011,553 B2 | 9/2011 | Mastri |
| 8,016,177 B2 | 9/2011 | Bettuchi |
| 8,021,378 B2 | 9/2011 | Sixto, Jr. |
| 8,028,884 B2 | 10/2011 | Sniffin |
| 8,033,439 B2 | 10/2011 | Racenet |
| 8,038,045 B2 | 10/2011 | Bettuchi |
| 8,043,328 B2 | 10/2011 | Hahnen |
| 8,056,787 B2 | 11/2011 | Boudreaux |
| 8,066,168 B2 | 11/2011 | Vidal |
| 8,066,721 B2 | 11/2011 | Kortenbach |
| 8,070,033 B2 | 12/2011 | Milliman |
| 8,070,035 B2 | 12/2011 | Holsten |
| 8,070,038 B2 | 12/2011 | Kostrzewski |
| 8,074,861 B2 | 12/2011 | Ehrenfels |
| 8,074,862 B2 | 12/2011 | Shah |
| 8,080,020 B2 | 12/2011 | Kortenbach |
| 8,080,032 B2 | 12/2011 | Van Der Burg |
| 8,083,118 B2 | 12/2011 | Milliman |
| 8,083,119 B2 | 12/2011 | Prommersberger |
| 8,091,753 B2 | 1/2012 | Viola |
| 8,091,756 B2 | 1/2012 | Frank |
| 8,096,459 B2 | 1/2012 | Ortiz |
| 8,097,015 B2 | 1/2012 | Devellian |
| 8,113,405 B2 | 2/2012 | Milliman |
| 8,113,406 B2 | 2/2012 | Holsten |
| 8,113,407 B2 | 2/2012 | Holsten |
| 8,113,408 B2 | 2/2012 | Wenchell |
| 8,114,123 B2 | 2/2012 | Brenzel |
| 8,118,207 B2 | 2/2012 | Racenet |
| 8,123,101 B2 | 2/2012 | Racenet |
| 8,128,642 B2 | 3/2012 | Heeps |
| 8,152,041 B2 | 4/2012 | Kostrzewski |
| 8,152,823 B2 | 4/2012 | Kassab |
| 8,157,149 B2 | 4/2012 | Olson |
| 8,157,152 B2 | 4/2012 | Holsten |
| 8,162,197 B2 | 4/2012 | Mastri |
| 8,172,122 B2 | 5/2012 | Kasvikis |
| 8,181,837 B2 | 5/2012 | Roy |
| 8,186,558 B2 | 5/2012 | Sapienza |
| 8,187,286 B2 | 5/2012 | Jugenheimer |
| 8,191,752 B2 | 6/2012 | Scirica |
| 8,192,460 B2 | 6/2012 | Orban, III |
| 8,196,796 B2 | 6/2012 | Shelton, IV |
| 8,205,620 B2 | 6/2012 | Taylor |
| 8,205,780 B2 | 6/2012 | Sorrentino |
| 8,205,781 B2 | 6/2012 | Baxter, III |
| 8,210,412 B2 | 7/2012 | Marczyk |
| 8,210,413 B2 | 7/2012 | Whitman |
| 8,210,414 B2 | 7/2012 | Bettuchi |
| 8,210,416 B2 | 7/2012 | Milliman |
| 8,215,532 B2 | 7/2012 | Marczyk |
| 8,220,690 B2 | 7/2012 | Hess |
| 8,221,445 B2 | 7/2012 | Van Tassel |
| 8,225,980 B1 | 7/2012 | Rivera |
| 8,231,040 B2 | 7/2012 | Zemlok |
| 8,235,272 B2 | 8/2012 | Nicholas |
| 8,235,274 B2 | 8/2012 | Cappola |
| 8,236,015 B2 | 8/2012 | Bettuchi |
| 8,240,536 B2 | 8/2012 | Marczyk |
| 8,240,537 B2 | 8/2012 | Marczyk |
| 8,241,322 B2 | 8/2012 | Whitman |
| 8,245,900 B2 | 8/2012 | Scirica |
| 8,245,901 B2 | 8/2012 | Stopek |
| 8,246,634 B2 | 8/2012 | Huitema |
| 8,256,654 B2 | 9/2012 | Bettuchi |
| 8,256,655 B2 | 9/2012 | Sniffin |
| 8,256,656 B2 | 9/2012 | Milliman |
| 8,267,849 B2 | 9/2012 | Wazer |
| 8,272,552 B2 | 9/2012 | Holsten |
| 8,272,553 B2 | 9/2012 | Mastri |
| 8,272,554 B2 | 9/2012 | Whitman |
| 8,276,594 B2 | 10/2012 | Shah |
| 8,276,800 B2 | 10/2012 | Bettuchi |
| 8,276,801 B2 | 10/2012 | Zemlok |
| 8,276,802 B2 | 10/2012 | Kostrzewski |
| 8,281,973 B2 | 10/2012 | Wenchell |
| 8,281,974 B2 | 10/2012 | Hessler |
| 8,281,975 B2 | 10/2012 | Criscuolo |
| 8,286,847 B2 | 10/2012 | Taylor |
| 8,286,848 B2 | 10/2012 | Wenchell |
| 8,287,563 B2 | 10/2012 | Khairkhahan |
| 8,292,146 B2 | 10/2012 | Holsten |
| 8,292,147 B2 | 10/2012 | Viola |

(56) References Cited

U.S. PATENT DOCUMENTS

| | | |
|---|---|---|
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman |
| 8,292,153 B2 | 10/2012 | Jankowski |
| 8,292,154 B2 | 10/2012 | Marczyk |
| 8,292,155 B2 | 10/2012 | Shelton, IV |
| 8,292,156 B2 | 10/2012 | Kostrzewski |
| 8,292,158 B2 | 10/2012 | Sapienza |
| 8,403,197 B2 | 3/2013 | Viola |
| 8,561,872 B2 | 10/2013 | Wheeler |
| 8,647,350 B2 | 2/2014 | Mohan |
| 8,685,055 B2 | 4/2014 | Vantassel |
| 9,072,536 B2 | 7/2015 | Shelton, IV |
| 9,232,941 B2 | 1/2016 | Mandakolathur Vasudevan |
| 9,289,211 B2 | 3/2016 | Williams |
| 9,375,218 B2 | 6/2016 | Wheeler |
| 9,861,359 B2 | 1/2018 | Shelton, IV |
| 10,595,861 B2 | 3/2020 | Wheeler |
| 2001/0005787 A1 | 6/2001 | Oz |
| 2001/0014811 A1 | 8/2001 | Hussein |
| 2001/0016748 A1 | 8/2001 | Tanner |
| 2001/0034536 A1 | 10/2001 | Looper |
| 2001/0039423 A1 | 11/2001 | Skiba |
| 2001/0041914 A1 | 11/2001 | Frazier |
| 2002/0022860 A1 | 2/2002 | Borillo |
| 2002/0022880 A1 | 2/2002 | Melvin |
| 2002/0032454 A1 | 3/2002 | Durgin |
| 2002/0047035 A1 | 4/2002 | Coleman |
| 2002/0049457 A1 | 4/2002 | Kaplan |
| 2002/0055750 A1 | 5/2002 | Durgin |
| 2002/0065535 A1 | 5/2002 | Kneifel |
| 2002/0068945 A1 | 6/2002 | Robert |
| 2002/0072759 A1 | 6/2002 | Fry |
| 2002/0082621 A1 | 6/2002 | Schurr |
| 2002/0103492 A1 | 8/2002 | Kaplan |
| 2002/0111637 A1 | 8/2002 | Kaplan |
| 2002/0120281 A1 | 8/2002 | Overaker |
| 2002/0138086 A1 | 9/2002 | Robert |
| 2002/0151889 A1 | 10/2002 | Swanson |
| 2002/0173848 A1 | 11/2002 | Sachs |
| 2002/0177863 A1 | 11/2002 | Mandel |
| 2002/0183770 A1 | 12/2002 | Anderson |
| 2002/0183771 A1 | 12/2002 | Burbank |
| 2002/0183785 A1 | 12/2002 | Howell |
| 2002/0198549 A1 | 12/2002 | Robert |
| 2003/0023266 A1 | 1/2003 | Borillo |
| 2003/0065340 A1 | 4/2003 | Geitz |
| 2003/0078603 A1 | 4/2003 | Schaller |
| 2003/0114865 A1 | 6/2003 | Sater |
| 2003/0120337 A1 | 6/2003 | Van Tassel |
| 2003/0125729 A1 | 7/2003 | Hooven |
| 2003/0125755 A1 | 7/2003 | Schaller |
| 2003/0130670 A1 | 7/2003 | Anderson |
| 2003/0153930 A1 | 8/2003 | De Canniere |
| 2003/0158464 A1 | 8/2003 | Bertolero |
| 2003/0158604 A1 | 8/2003 | Cauthen |
| 2003/0181929 A1 | 9/2003 | Geitz |
| 2003/0191479 A1 | 10/2003 | Thornton |
| 2003/0191494 A1 | 10/2003 | Gray |
| 2003/0191526 A1 | 10/2003 | Van Tassel |
| 2003/0195531 A1 | 10/2003 | Gardiner |
| 2003/0216757 A1 | 11/2003 | Gerberding |
| 2003/0220660 A1 | 11/2003 | Kortenbach |
| 2003/0220667 A1 | 11/2003 | van der Burg |
| 2003/0225421 A1 | 12/2003 | Peavey |
| 2003/0225423 A1 | 12/2003 | Huitema |
| 2003/0225424 A1 | 12/2003 | Benderev |
| 2003/0229367 A1 | 12/2003 | Viola |
| 2003/0233095 A1 | 12/2003 | Urbanski |
| 2003/0236537 A1 | 12/2003 | Hart |
| 2004/0006353 A1 | 1/2004 | Bosley |
| 2004/0024414 A1 | 2/2004 | Downing |
| 2004/0030335 A1 | 2/2004 | Zenati |
| 2004/0034375 A1 | 2/2004 | Ruiz |
| 2004/0049210 A1 | 3/2004 | Vantassel |
| 2004/0059354 A1 | 3/2004 | Smith |
| 2004/0059359 A1 | 3/2004 | Wilson |
| 2004/0073234 A1 | 4/2004 | Chu |
| 2004/0073241 A1 | 4/2004 | Barry |
| 2004/0089312 A1 | 5/2004 | Jordan |
| 2004/0092973 A1 | 5/2004 | Chanduszko |
| 2004/0093024 A1 | 5/2004 | Lousararian |
| 2004/0097980 A1 | 5/2004 | Ferree |
| 2004/0097982 A1 | 5/2004 | Jugenheimer |
| 2004/0111100 A1 | 6/2004 | Benderev |
| 2004/0116948 A1 | 6/2004 | Robert |
| 2004/0122456 A1 | 6/2004 | Saadat |
| 2004/0122467 A1 | 6/2004 | Vantassel |
| 2004/0127919 A1 | 7/2004 | Hugh |
| 2004/0127935 A1 | 7/2004 | Vantassel |
| 2004/0133214 A1 | 7/2004 | Kayan |
| 2004/0133215 A1 | 7/2004 | Baxter |
| 2004/0133219 A1 | 7/2004 | Forsell |
| 2004/0138683 A1 | 7/2004 | Shelton |
| 2004/0186486 A1 | 9/2004 | Roue |
| 2004/0193188 A1 | 9/2004 | Francese |
| 2004/0199178 A1 | 10/2004 | Small |
| 2004/0230222 A1 | 11/2004 | Van Der Burg |
| 2004/0260314 A1 | 12/2004 | Lizardi |
| 2005/0004652 A1 | 1/2005 | Van Der Burg |
| 2005/0021061 A1 | 1/2005 | Dennis |
| 2005/0021062 A1 | 1/2005 | Dennis |
| 2005/0027308 A1 | 2/2005 | Davis |
| 2005/0049573 A1 | 3/2005 | Van Tassel |
| 2005/0059988 A1 | 3/2005 | Danitz |
| 2005/0125010 A1 | 6/2005 | Smith |
| 2005/0139635 A1 | 6/2005 | Wukusick |
| 2005/0143767 A1 | 6/2005 | Kimura |
| 2005/0146069 A1 | 7/2005 | Kanan |
| 2005/0149068 A1 | 7/2005 | Williams |
| 2005/0149069 A1 | 7/2005 | Bertolero |
| 2005/0149988 A1 | 7/2005 | Grannan |
| 2005/0149989 A1 | 7/2005 | Lupoi |
| 2005/0154404 A1 | 7/2005 | Liddicoat |
| 2005/0165421 A1 | 7/2005 | Wilson |
| 2005/0165422 A1 | 7/2005 | Wilson |
| 2005/0165423 A1 | 7/2005 | Gallagher |
| 2005/0165424 A1 | 7/2005 | Gallagher |
| 2005/0171560 A1 | 8/2005 | Hughett |
| 2005/0177180 A1 | 8/2005 | Kaganov |
| 2005/0177182 A1 | 8/2005 | Van Der Burg |
| 2005/0177224 A1 | 8/2005 | Fogarty |
| 2005/0177232 A1 | 8/2005 | Ashton |
| 2005/0187569 A1 | 8/2005 | Dahl |
| 2005/0234543 A1 | 10/2005 | Glaser |
| 2005/0251184 A1 | 11/2005 | Anderson |
| 2005/0273122 A1 | 12/2005 | Theroux |
| 2005/0277955 A1 | 12/2005 | Palmer |
| 2005/0277959 A1 | 12/2005 | Cosgrove |
| 2006/0004388 A1 | 1/2006 | Whayne |
| 2006/0004390 A1 | 1/2006 | Rosenberg |
| 2006/0020162 A1 | 1/2006 | Whayne |
| 2006/0020271 A1 | 1/2006 | Stewart |
| 2006/0020275 A1 | 1/2006 | Goldfarb |
| 2006/0025812 A1 | 2/2006 | Shelton |
| 2006/0100644 A1 | 5/2006 | Mola |
| 2006/0100649 A1 | 5/2006 | Hart |
| 2006/0111735 A1 | 5/2006 | Crainich |
| 2006/0151567 A1 | 7/2006 | Roy |
| 2006/0217749 A1 | 9/2006 | Wilson |
| 2006/0264979 A1 | 11/2006 | Shepard |
| 2006/0264987 A1 | 11/2006 | Sgro |
| 2007/0005108 A1 | 1/2007 | Simhon |
| 2007/0016228 A1 | 1/2007 | Salas |
| 2007/0060951 A1 | 3/2007 | Shannon |
| 2007/0073274 A1 | 3/2007 | Chin |
| 2007/0083218 A1 | 4/2007 | Steven |
| 2007/0083227 A1 | 4/2007 | Van Der Burg |
| 2007/0106314 A1 | 5/2007 | Dunn |
| 2007/0112365 A1 | 5/2007 | Hilal |
| 2007/0118161 A1 | 5/2007 | Kennedy |
| 2007/0118163 A1 | 5/2007 | Boudreaux |

(56) References Cited

U.S. PATENT DOCUMENTS

| | | |
|---|---|---|
| 2007/0135826 A1 | 6/2007 | Zaver |
| 2007/0149988 A1 | 6/2007 | Michler |
| 2007/0149989 A1 | 6/2007 | Santilli |
| 2007/0149995 A1 | 6/2007 | Quinn |
| 2007/0162060 A1 | 7/2007 | Wild |
| 2007/0167964 A1 | 7/2007 | Willis |
| 2007/0179512 A1 | 8/2007 | Olsen |
| 2007/0185506 A1 | 8/2007 | Jackson |
| 2007/0191868 A1 | 8/2007 | Theroux |
| 2007/0203391 A1 | 8/2007 | Bloom |
| 2007/0208357 A1 | 9/2007 | Houser |
| 2007/0213747 A1 | 9/2007 | Monassevitch |
| 2007/0246505 A1 | 10/2007 | Pace-Floridia |
| 2007/0250086 A1 | 10/2007 | Wiley |
| 2007/0260278 A1 | 11/2007 | Wheeler |
| 2007/0265640 A1 | 11/2007 | Kortenbach |
| 2007/0265641 A1 | 11/2007 | Roue |
| 2007/0265642 A1 | 11/2007 | Chanduszko |
| 2007/0270891 A1 | 11/2007 | McGuckin |
| 2007/0276417 A1 | 11/2007 | Mendes, Jr. |
| 2007/0299469 A1 | 12/2007 | Carpenter |
| 2008/0009866 A1 | 1/2008 | Alamin |
| 2008/0021466 A1 | 1/2008 | Shadduck |
| 2008/0021484 A1 | 1/2008 | Catanese |
| 2008/0027471 A1 | 1/2008 | Hauri |
| 2008/0027478 A1 | 1/2008 | Connors |
| 2008/0033241 A1 | 2/2008 | Peh |
| 2008/0033457 A1 | 2/2008 | Francischelli |
| 2008/0039879 A1 | 2/2008 | Chin |
| 2008/0039922 A1 | 2/2008 | Miles |
| 2008/0060658 A1 | 3/2008 | Doorschodt |
| 2008/0071294 A1 | 3/2008 | Bender |
| 2008/0078800 A1 | 4/2008 | Hess |
| 2008/0078802 A1 | 4/2008 | Hess |
| 2008/0078803 A1 | 4/2008 | Shelton |
| 2008/0078804 A1 | 4/2008 | Shelton |
| 2008/0078806 A1 | 4/2008 | Omaits |
| 2008/0078808 A1 | 4/2008 | Hess |
| 2008/0097571 A1 | 4/2008 | Denison |
| 2008/0105265 A1 | 5/2008 | Pannell |
| 2008/0125795 A1 | 5/2008 | Kaplan |
| 2008/0125796 A1 | 5/2008 | Graham |
| 2008/0132891 A1 | 6/2008 | Nobis |
| 2008/0140095 A1 | 6/2008 | Smith |
| 2008/0147083 A1 | 6/2008 | Vold |
| 2008/0177292 A1 | 7/2008 | Jacobs |
| 2008/0183283 A1 | 7/2008 | Downing |
| 2008/0208324 A1 | 8/2008 | Glithero |
| 2008/0215090 A1 | 9/2008 | Gonzales |
| 2008/0234785 A1 | 9/2008 | Nakayama |
| 2008/0249547 A1 | 10/2008 | Dunn |
| 2008/0269787 A1 | 10/2008 | Laufer |
| 2008/0287989 A1 | 11/2008 | Weisel |
| 2008/0294179 A1 | 11/2008 | Balbierz |
| 2008/0300686 A1 | 12/2008 | Khoo |
| 2008/0312670 A1 | 12/2008 | Lutze |
| 2008/0314956 A1 | 12/2008 | Boudreaux |
| 2008/0314961 A1 | 12/2008 | Boudreaux |
| 2008/0319456 A1 | 12/2008 | Hart |
| 2009/0001121 A1 | 1/2009 | Hess |
| 2009/0001124 A1 | 1/2009 | Hess |
| 2009/0005808 A1 | 1/2009 | Hess |
| 2009/0012545 A1 | 1/2009 | Williamson, IV |
| 2009/0020584 A1 | 1/2009 | Soltz |
| 2009/0048665 A1 | 2/2009 | Miron |
| 2009/0054916 A1 | 2/2009 | Meier |
| 2009/0088783 A1 | 4/2009 | Kennedy |
| 2009/0093826 A1 | 4/2009 | Warder-Gabaldon |
| 2009/0105731 A1 | 4/2009 | Priewe |
| 2009/0112249 A1 | 4/2009 | Miles |
| 2009/0118748 A1 | 5/2009 | Pugsley |
| 2009/0131959 A1 | 5/2009 | Rolland |
| 2009/0138028 A1 | 5/2009 | Wells |
| 2009/0163937 A1 | 6/2009 | Kassab |
| 2009/0171380 A1 | 7/2009 | Whiting |
| 2009/0171386 A1 | 7/2009 | Amplatz |
| 2009/0177212 A1 | 7/2009 | Carley |
| 2009/0182326 A1 | 7/2009 | Zenati |
| 2009/0182374 A1 | 7/2009 | Keith |
| 2009/0182419 A1 | 7/2009 | Bolling |
| 2009/0187198 A1 | 7/2009 | Weitzner |
| 2009/0206127 A1 | 8/2009 | Danielson |
| 2009/0209986 A1 | 8/2009 | Stewart |
| 2009/0222025 A1 | 9/2009 | Joseph, III |
| 2009/0240267 A1 | 9/2009 | Crawley |
| 2009/0240268 A1 | 9/2009 | Kassab |
| 2009/0264880 A1 | 10/2009 | Solem |
| 2009/0277948 A1 | 11/2009 | Beardsley |
| 2010/0023023 A1 | 1/2010 | Popovic |
| 2010/0063541 A1 | 3/2010 | Brunelle |
| 2010/0069924 A1 | 3/2010 | Kochman |
| 2010/0069928 A1 | 3/2010 | Bauer |
| 2010/0069930 A1 | 3/2010 | Roslin |
| 2010/0082047 A1 | 4/2010 | Cosgrove |
| 2010/0114124 A1 | 5/2010 | Kelleher |
| 2010/0114133 A1 | 5/2010 | Huitema |
| 2010/0114134 A1 | 5/2010 | Mcintyre |
| 2010/0114157 A1 | 5/2010 | Sabanathan |
| 2010/0115739 A1 | 5/2010 | Mathur |
| 2010/0121359 A1 | 5/2010 | Atui |
| 2010/0125288 A1 | 5/2010 | Gelfand |
| 2010/0130965 A1 | 5/2010 | Sibbitt, Jr. |
| 2010/0137885 A1 | 6/2010 | Ortiz |
| 2010/0145361 A1 | 6/2010 | Francischelli |
| 2010/0155453 A1 | 6/2010 | Bombard |
| 2010/0163054 A1 | 7/2010 | Breznel |
| 2010/0168791 A1 | 7/2010 | Kassab |
| 2010/0179570 A1 | 7/2010 | Privitera |
| 2010/0185219 A1 | 7/2010 | Gertzman |
| 2010/0185221 A1 | 7/2010 | Shipp |
| 2010/0186750 A1 | 7/2010 | Tran |
| 2010/0191257 A1 | 7/2010 | Boulnois |
| 2010/0191279 A1 | 7/2010 | Kassab |
| 2010/0204716 A1 | 8/2010 | Stewart |
| 2010/0211046 A1 | 8/2010 | Adams |
| 2010/0217314 A1 | 8/2010 | Holsten |
| 2010/0222789 A1 | 9/2010 | Gelbart |
| 2010/0228269 A1 | 9/2010 | Garrison |
| 2010/0228279 A1 | 9/2010 | Miles |
| 2010/0228285 A1 | 9/2010 | Miles |
| 2010/0234862 A1 | 9/2010 | Patel |
| 2010/0241139 A1 | 9/2010 | Harshman |
| 2010/0256660 A1 | 10/2010 | Anderson |
| 2010/0264194 A1* | 10/2010 | Huang ............ A61B 17/07207 227/180.1 |
| 2010/0286718 A1 | 11/2010 | Kassab |
| 2010/0292713 A1 | 11/2010 | Cohn |
| 2010/0292719 A1 | 11/2010 | Ducharme |
| 2010/0324572 A1 | 12/2010 | Needleman |
| 2010/0324585 A1 | 12/2010 | Miles |
| 2010/0324586 A1 | 12/2010 | Miles |
| 2010/0324587 A1 | 12/2010 | Miles |
| 2010/0324588 A1 | 12/2010 | Miles |
| 2010/0331862 A1 | 12/2010 | Monassevitch |
| 2010/0331880 A1 | 12/2010 | Stopek |
| 2011/0009853 A1 | 1/2011 | Bertolero |
| 2011/0022079 A1 | 1/2011 | Miles |
| 2011/0036896 A1 | 2/2011 | Buesseler |
| 2011/0046437 A1 | 2/2011 | Kassab |
| 2011/0046641 A1 | 2/2011 | Kassab |
| 2011/0054515 A1 | 3/2011 | Bridgeman |
| 2011/0068143 A1 | 3/2011 | Laufer |
| 2011/0071547 A1 | 3/2011 | Mcbrayer |
| 2011/0071555 A1 | 3/2011 | Mcbrayer |
| 2011/0082495 A1 | 4/2011 | Ruiz |
| 2011/0112559 A1 | 5/2011 | Monassevitch |
| 2011/0125171 A1 | 5/2011 | Mola |
| 2011/0144661 A1 | 6/2011 | Houser |
| 2011/0152895 A1 | 6/2011 | Nyuli |
| 2011/0155788 A1 | 6/2011 | Hillstead |
| 2011/0174863 A1 | 7/2011 | Shelton, IV |
| 2011/0178534 A1 | 7/2011 | Whitman |
| 2011/0178535 A1 | 7/2011 | Whitman |
| 2011/0178539 A1 | 7/2011 | Holmes, Jr. |

(56) References Cited

U.S. PATENT DOCUMENTS

| | | |
|---|---|---|
| 2011/0190791 A1 | 8/2011 | Jacobs |
| 2011/0190809 A1 | 8/2011 | Mohan |
| 2011/0208233 A1 | 8/2011 | Mcguckin, Jr. |
| 2011/0218566 A1 | 9/2011 | Van Der Burg |
| 2011/0224700 A1 | 9/2011 | Schmidt |
| 2011/0224701 A1 | 9/2011 | Menn |
| 2011/0230903 A1 | 9/2011 | Bertolero |
| 2011/0238094 A1 | 9/2011 | Thomas |
| 2011/0245849 A1 | 10/2011 | Jabba |
| 2011/0270285 A1 | 11/2011 | Lissa |
| 2011/0270303 A1 | 11/2011 | Wheeler |
| 2011/0295290 A1 | 12/2011 | Whitfield |
| 2011/0295291 A1 | 12/2011 | Trivisani |
| 2011/0313437 A1 | 12/2011 | Yeh |
| 2012/0010635 A1 | 1/2012 | Yeretsian |
| 2012/0035631 A1 | 2/2012 | Hughett, Sr. |
| 2012/0035643 A1 | 2/2012 | Khairkhahan |
| 2012/0059400 A1 | 3/2012 | Williamson, IV |
| 2012/0065662 A1 | 3/2012 | Van Der Burg |
| 2012/0065667 A1 | 3/2012 | Javois |
| 2012/0071918 A1 | 3/2012 | Amin |
| 2012/0074198 A1 | 3/2012 | Huitema |
| 2012/0080478 A1 | 4/2012 | Morgan |
| 2012/0080479 A1 | 4/2012 | Shelton, IV |
| 2012/0080480 A1 | 4/2012 | Woodard, Jr. |
| 2012/0080481 A1 | 4/2012 | Widenhouse |
| 2012/0080482 A1 | 4/2012 | Schall |
| 2012/0080483 A1 | 4/2012 | Riestenberg |
| 2012/0080484 A1 | 4/2012 | Morgan |
| 2012/0080485 A1 | 4/2012 | Woodard, Jr. |
| 2012/0080486 A1 | 4/2012 | Woodard, Jr. |
| 2012/0080487 A1 | 4/2012 | Woodard, Jr. |
| 2012/0080488 A1 | 4/2012 | Shelton, IV |
| 2012/0080489 A1 | 4/2012 | Shelton, IV |
| 2012/0080490 A1 | 4/2012 | Shelton, IV |
| 2012/0080491 A1 | 4/2012 | Shelton, IV |
| 2012/0080503 A1 | 4/2012 | Woodard, Jr. |
| 2012/0083803 A1 | 4/2012 | Patel |
| 2012/0093903 A1 | 4/2012 | Roth |
| 2012/0101509 A1 | 4/2012 | Paganon |
| 2012/0109161 A1 | 5/2012 | Privitera |
| 2012/0111920 A1 | 5/2012 | Kostrzewski |
| 2012/0123445 A1 | 5/2012 | Hughett, Sr. |
| 2012/0130402 A1 | 5/2012 | Heeps |
| 2012/0130421 A1 | 5/2012 | Hafez |
| 2012/0145767 A1 | 6/2012 | Shah |
| 2012/0145768 A1 | 6/2012 | Sorrentino |
| 2012/0158022 A1 | 6/2012 | Kaplan |
| 2012/0160890 A1 | 6/2012 | Holcomb |
| 2012/0172927 A1 | 7/2012 | Campbell |
| 2012/0209297 A1 | 8/2012 | Jugenheimer |
| 2012/0228359 A1 | 9/2012 | Frank |
| 2012/0239083 A1 | 9/2012 | Kreidler |
| 2012/0241503 A1 | 9/2012 | Baxter, III |
| 2012/0241505 A1 | 9/2012 | Alexander, III |
| 2012/0245605 A1 | 9/2012 | Nicholson, IV |
| 2012/0248169 A1 | 10/2012 | Widenhouse |
| 2012/0271337 A1 | 10/2012 | Figulla |
| 2012/0283585 A1 | 11/2012 | Werneth |
| 2012/0283773 A1 | 11/2012 | Van Tassel |
| 2013/0023911 A1 | 1/2013 | Esanu |
| 2014/0163605 A1 | 6/2014 | Vantassel |
| 2015/0129634 A1 | 5/2015 | Shelton, IV |
| 2015/0164524 A1 | 6/2015 | Malkowski |
| 2015/0223807 A1 | 8/2015 | Mohan |
| 2016/0270784 A1 | 9/2016 | Wheeler |
| 2016/0296233 A1 | 10/2016 | Wheeler |
| 2016/0317155 A1 | 11/2016 | Kimura et al. |

FOREIGN PATENT DOCUMENTS

| | | |
|---|---|---|
| DE | 19520158 A1 | 12/1996 |
| DE | 19534320 C1 | 2/1997 |
| DE | 19537299 A1 | 4/1997 |
| DE | 19707382 A1 | 9/1997 |
| DE | 29716753 U1 | 10/1997 |
| DE | 29715758 U1 | 1/1998 |
| DE | 29822558 U1 | 2/1999 |
| DE | 19738306 A1 | 3/1999 |
| DE | 19741053 A1 | 4/1999 |
| DE | 29913246 U1 | 9/1999 |
| DE | 19925304 A1 | 12/1999 |
| DE | 19832739 A1 | 2/2000 |
| DE | 19860685 A1 | 7/2000 |
| DE | 19858577 C1 | 9/2000 |
| DE | 19951940 A1 | 6/2001 |
| DE | 10212385 A1 | 11/2002 |
| DE | 20214068 U1 | 11/2002 |
| DE | 20208744 U1 | 1/2003 |
| DE | 10203946 A1 | 3/2003 |
| DE | 10347391 A1 | 5/2005 |
| DE | 102004015223 A1 | 10/2005 |
| DE | 102004026617 A1 | 12/2005 |
| DE | 202007003398 U1 | 6/2007 |
| DE | 102009018819 A1 | 10/2010 |
| DE | 102009018821 A1 | 10/2010 |
| DE | 202010008941 U1 | 12/2010 |
| DE | 202012001672 U1 | 3/2012 |
| DE | 102010060322 A1 | 5/2012 |
| EP | 138687 A1 | 4/1985 |
| EP | 0169044 A2 | 1/1986 |
| EP | 0314064 A2 | 5/1989 |
| EP | 324549 A2 | 7/1989 |
| EP | 476523 A2 | 3/1992 |
| EP | 489436 A1 | 6/1992 |
| EP | 0490411 | 6/1992 |
| EP | 492283 A1 | 7/1992 |
| EP | 0510826 | 10/1992 |
| EP | 537572 A2 | 4/1993 |
| EP | 567965 A2 | 11/1993 |
| EP | 576835 A2 | 1/1994 |
| EP | 578425 A1 | 1/1994 |
| EP | 0594002 A1 | 4/1994 |
| EP | 0594004 A1 | 4/1994 |
| EP | 598976 A2 | 6/1994 |
| EP | 0600182 A2 | 6/1994 |
| EP | 0609612 | 8/1994 |
| EP | 0610307 A1 | 8/1994 |
| EP | 674876 A2 | 10/1995 |
| EP | 676173 A1 | 10/1995 |
| EP | 0681810 | 11/1995 |
| EP | 696179 A1 | 2/1996 |
| EP | 699415 A2 | 3/1996 |
| EP | 0704190 A1 | 4/1996 |
| EP | 714633 A1 | 6/1996 |
| EP | 0724405 | 8/1996 |
| EP | 754433 A2 | 1/1997 |
| EP | 758214 A1 | 2/1997 |
| EP | 763346 A1 | 3/1997 |
| EP | 763347 A1 | 3/1997 |
| EP | 0780107 | 6/1997 |
| EP | 0790804 | 8/1997 |
| EP | 793944 A1 | 9/1997 |
| EP | 885595 A1 | 12/1998 |
| EP | 0893970 | 2/1999 |
| EP | 897696 A1 | 2/1999 |
| EP | 0910293 | 4/1999 |
| EP | 981296 A1 | 3/2000 |
| EP | 1064883 A1 | 1/2001 |
| EP | 1072225 A2 | 1/2001 |
| EP | 1090592 A1 | 4/2001 |
| EP | 1100382 A1 | 5/2001 |
| EP | 1199990 A1 | 5/2002 |
| EP | 1233708 A2 | 8/2002 |
| EP | 1250096 A2 | 10/2002 |
| EP | 1254636 A2 | 11/2002 |
| EP | 1256317 A1 | 11/2002 |
| EP | 1289428 A2 | 3/2003 |
| EP | 1289432 A1 | 3/2003 |
| EP | 1326544 A1 | 7/2003 |
| EP | 1339327 A2 | 9/2003 |
| EP | 1342451 A1 | 9/2003 |
| EP | 1357843 B1 | 11/2003 |
| EP | 1389065 B1 | 2/2004 |

(56) References Cited

FOREIGN PATENT DOCUMENTS

| | | |
|---|---|---|
| EP | 1399072 B1 | 3/2004 |
| EP | 1417933 | 5/2004 |
| EP | 1418848 B1 | 5/2004 |
| EP | 1437972 B1 | 7/2004 |
| EP | 1455653 B1 | 9/2004 |
| EP | 1462061 A2 | 9/2004 |
| EP | 1462062 A2 | 9/2004 |
| EP | 1465532 B1 | 10/2004 |
| EP | 1492460 B1 | 1/2005 |
| EP | 1545332 B1 | 6/2005 |
| EP | 1545333 B1 | 6/2005 |
| EP | 1600108 A2 | 11/2005 |
| EP | 1603465 B1 | 12/2005 |
| EP | 1684641 B1 | 8/2006 |
| EP | 1694218 A2 | 8/2006 |
| EP | 1709915 A1 | 10/2006 |
| EP | 1723914 A1 | 11/2006 |
| EP | 1757235 A1 | 2/2007 |
| EP | 1767157 A1 | 3/2007 |
| EP | 1774914 A1 | 4/2007 |
| EP | 1774915 A1 | 4/2007 |
| EP | 1810622 A1 | 7/2007 |
| EP | 1813214 A1 | 8/2007 |
| EP | 1815803 A1 | 8/2007 |
| EP | 1829489 A1 | 9/2007 |
| EP | 1852141 A2 | 11/2007 |
| EP | 1874196 B1 | 1/2008 |
| EP | 1908412 A2 | 4/2008 |
| EP | 1908413 A1 | 4/2008 |
| EP | 1908415 A1 | 4/2008 |
| EP | 1913881 A1 | 4/2008 |
| EP | 1949863 A1 | 7/2008 |
| EP | 1971276 B1 | 9/2008 |
| EP | 1980214 A2 | 10/2008 |
| EP | 1983906 B1 | 10/2008 |
| EP | 1993451 B1 | 11/2008 |
| EP | 2010066 B1 | 1/2009 |
| EP | 2019633 B1 | 2/2009 |
| EP | 2044892 A2 | 4/2009 |
| EP | 2074954 A1 | 7/2009 |
| EP | 2098170 A2 | 9/2009 |
| EP | 2098175 A1 | 9/2009 |
| EP | 2110082 A1 | 10/2009 |
| EP | 2110083 A2 | 10/2009 |
| EP | 2110084 A2 | 10/2009 |
| EP | 2113209 A1 | 11/2009 |
| EP | 2116193 A1 | 11/2009 |
| EP | 2116194 A2 | 11/2009 |
| EP | 2116195 A1 | 11/2009 |
| EP | 2130501 A1 | 12/2009 |
| EP | 2151204 A1 | 2/2010 |
| EP | 2158854 A1 | 3/2010 |
| EP | 2241265 A1 | 10/2010 |
| EP | 2253279 A1 | 11/2010 |
| EP | 2286737 A1 | 2/2011 |
| EP | 2316351 A2 | 5/2011 |
| EP | 2328482 A1 | 6/2011 |
| EP | 2347722 A1 | 7/2011 |
| EP | 2380509 A2 | 10/2011 |
| EP | 2389878 A1 | 11/2011 |
| EP | 2392268 A1 | 12/2011 |
| EP | 2409654 A2 | 1/2012 |
| EP | 2412318 A2 | 2/2012 |
| EP | 2417916 A2 | 2/2012 |
| EP | 2446838 A2 | 5/2012 |
| EP | 2455007 A2 | 5/2012 |
| EP | 2455012 A2 | 5/2012 |
| EP | 2462880 A2 | 6/2012 |
| EP | 2497431 A1 | 9/2012 |
| EP | 2520228 A2 | 11/2012 |
| EP | 3120781 | 1/2017 |
| FR | 2598905 A1 | 11/1987 |
| FR | 2815842 A1 | 5/2002 |
| GB | 1530282 A | 10/1978 |
| GB | 2150440 A | 7/1985 |
| GB | 2177748 A | 1/1987 |
| GB | 2190297 A | 11/1987 |
| GB | 2226958 A | 7/1990 |
| GB | 2443736 A | 5/2008 |
| JP | S58190432 | 11/1983 |
| JP | S60501392 | 8/1985 |
| JP | S62246357 | 10/1987 |
| JP | 3336540 | 10/1993 |
| JP | H08336540 | 12/1996 |
| JP | 2005-13732 A | 1/2005 |
| JP | 2006507042 A | 3/2006 |
| JP | 2007535997 | 12/2007 |
| JP | 2009536082 A | 10/2009 |
| JP | 2015-195837 A | 11/2015 |
| RU | 2093201 C1 | 10/1996 |
| RU | 2110221 C1 | 5/1998 |
| RU | 2196530 C1 | 1/2003 |
| RU | 2245113 C2 | 1/2005 |
| RU | 2261057 C1 | 9/2005 |
| RU | 2299023 C2 | 1/2007 |
| RU | 2008141508 | 5/2010 |
| WO | 1993009717 A1 | 5/1993 |
| WO | 9415535 | 7/1994 |
| WO | 1996002279 A2 | 2/1996 |
| WO | 1996019146 A1 | 6/1996 |
| WO | 9846301 | 10/1998 |
| WO | 9913780 A1 | 3/1999 |
| WO | 9920183 | 4/1999 |
| WO | 1999018858 A1 | 4/1999 |
| WO | 2000032113 A1 | 6/2000 |
| WO | 2000054662 A1 | 9/2000 |
| WO | 0110306 | 2/2001 |
| WO | 2001028432 A1 | 4/2001 |
| WO | 2001043649 A1 | 6/2001 |
| WO | 0224080 A2 | 3/2002 |
| WO | 2002017809 A1 | 3/2002 |
| WO | 2002082975 A2 | 10/2002 |
| WO | 2002087425 A2 | 11/2002 |
| WO | 2003011150 A1 | 2/2003 |
| WO | 2003022159 A1 | 3/2003 |
| WO | 2003037162 A2 | 5/2003 |
| WO | 2003041596 A1 | 5/2003 |
| WO | 2003053256 A1 | 7/2003 |
| WO | 2003082076 A2 | 10/2003 |
| WO | 2003082129 A2 | 10/2003 |
| WO | 2003086206 A1 | 10/2003 |
| WO | 03090633 A2 | 11/2003 |
| WO | 2003096881 A2 | 11/2003 |
| WO | 2004004542 A2 | 1/2004 |
| WO | 2004023976 A2 | 3/2004 |
| WO | 2004026148 A1 | 4/2004 |
| WO | 2004026201 A1 | 4/2004 |
| WO | 2004026350 A2 | 4/2004 |
| WO | 2004032761 A1 | 4/2004 |
| WO | 2004045370 A2 | 6/2004 |
| WO | 2004058079 A2 | 7/2004 |
| WO | 2004066846 A1 | 8/2004 |
| WO | 2004110285 A1 | 12/2004 |
| WO | 2005027721 A2 | 3/2005 |
| WO | 2005046453 A2 | 5/2005 |
| WO | 2005046453 A3 | 5/2005 |
| WO | 2005060838 A2 | 7/2005 |
| WO | 2005060838 A3 | 7/2005 |
| WO | 2005063133 A1 | 7/2005 |
| WO | 2005072105 A2 | 8/2005 |
| WO | 2005086824 A2 | 9/2005 |
| WO | 2005096960 A1 | 10/2005 |
| WO | 2005120326 A2 | 12/2005 |
| WO | 2006009545 A1 | 1/2006 |
| WO | 2006042110 A2 | 4/2006 |
| WO | 2006085389 A1 | 8/2006 |
| WO | 2006102578 A1 | 9/2006 |
| WO | 2006126979 A2 | 11/2006 |
| WO | 2007009099 A2 | 1/2007 |
| WO | 2007016288 A2 | 2/2007 |
| WO | 2007019268 A2 | 2/2007 |
| WO | 2007019321 A2 | 2/2007 |
| WO | 2007025014 A2 | 3/2007 |
| WO | 2006126979 A3 | 5/2007 |

(56) References Cited

FOREIGN PATENT DOCUMENTS

| | | | |
|---|---|---|---|
| WO | 2007090291 A1 | 8/2007 |
| WO | 2007106342 A2 | 9/2007 |
| WO | 2007131110 A2 | 11/2007 |
| WO | 2008020975 A2 | 2/2008 |
| WO | 2008024671 A2 | 2/2008 |
| WO | 2008024672 A2 | 2/2008 |
| WO | 2008033558 A2 | 3/2008 |
| WO | 2008070763 A1 | 6/2008 |
| WO | 2008137833 A2 | 11/2008 |
| WO | 2009005527 A1 | 1/2009 |
| WO | 2009094078 A2 | 7/2009 |
| WO | 2009108464 A1 | 9/2009 |
| WO | 2009129369 A1 | 10/2009 |
| WO | 2009135022 A1 | 11/2009 |
| WO | 2009136397 A2 | 11/2009 |
| WO | 2010006028 A1 | 1/2010 |
| WO | 2010011661 A1 | 1/2010 |
| WO | 2010055232 A1 | 5/2010 |
| WO | 2010080386 A2 | 7/2010 |
| WO | 2010091913 A1 | 8/2010 |
| WO | 2011019848 A1 | 2/2011 |
| WO | 2011025877 A1 | 3/2011 |
| WO | 2011028196 A2 | 3/2011 |
| WO | 2011050658 A1 | 5/2011 |
| WO | 2011057282 A2 | 5/2011 |
| WO | 2011060386 A2 | 5/2011 |
| WO | 2011066533 A1 | 6/2011 |
| WO | 2011078959 A1 | 6/2011 |
| WO | 2011081791 A1 | 7/2011 |
| WO | 2011083027 A1 | 7/2011 |
| WO | 2011091185 A1 | 7/2011 |
| WO | 2011112577 A1 | 9/2011 |
| WO | 2012021082 A2 | 2/2012 |
| WO | 2012021207 A1 | 2/2012 |
| WO | 2012048387 A1 | 4/2012 |
| WO | 2012064643 A1 | 5/2012 |
| WO | 2012125621 A1 | 9/2012 |
| WO | 2012129317 A2 | 9/2012 |

OTHER PUBLICATIONS

Amendment dated Jul. 22, 2011 for U.S. Appl. No. 13/117,863.
Office Action dated Dec. 7, 2010 for U.S. Appl. No. 11/744,135.
Response to final office action dated Aug. 1, 2012 for U.S. Appl. No. 11/155,305.
Response to office action dated Apil. 28, 2009 for U.S. Appl. No. 11/155,305.
Revised Brief on Appeal dated Sep. 7, 2010 for U.S. Appl. No. 11/003,696 (14 pages).
International Search Report and Written Opinion of PCT Patent Application No. PCT/US2010/045216, mailed Oct. 12, 2010, 8 pages total.
Office action dated Jan. 31, 2013 for U.S. Appl. No. 12/849,534.
Office action dated Feb. 24, 2012 for U.S. Appl. No. 13/180,373.
Salzberg, Sacha P., et al., Surgical left atrial appendage occlusion: evaluation of a novel device with magnetic resonance imaging, Eur. J. Cardiothoracic Surg., Aug. 6, 2008, 766-770, 34.
Supplemental EP Search Report dated Feb. 3, 2014 for EP Patent Application No. 07761828.8, 5 pages.
Burke, Redmond P., et al., "Improved Surgical Approach to Left Atrial Appendage Aneurysm", Journal of Cardiac Surgery, 1992, vol. 7, No. 2, pp. 104-107.
Johnson, W. Dudley, et al., "The left atrial appendage: our most lethal human attachment! Surgical implications", European Journal of Cardio-thoracic Surgery, 2000, vol. 17, pp. 718-722.
Cox, James L., "The surgical treatment of atrial fibrillation", J. Thorac. Cardiovasc. Surg., 1991, vol. 101, pp. 584-592.
Madden, John L., Md, "Resection of the Left Auricular Appendix", J.A.M.A., Jul. 2, 1949, vol. 140, No. 9, pp. 769-772.
Bonow, Robert O., et al., "Guidelines for the Management of Patients With Valvular Heart Disease: Executive Summary: A Report of the American College of Cardiology/American Heart Association Task Force on Practice Guidelines (Committee on Management of Patients With Valvular Heart Disease)", Circulation J.A.M.A., 1998, vol. 98, pp. 1949-1984.
Halperin, Jonathan L, Md, Facc, et al., "Obliteration of the Left Atrial Appendage for Prevention of Thromboembolism", Journal of the American College of Cardiology, 2003, vol. 42, No. 7, pp. 1259-1261.
Bohm, Jurgen, et al., "Surgical removal of atrial septal defect occlusion system-devices", European Journal of Cardio- thoracic Surgery, 1997, vol. 12, pp. 869-872.
Stollberger, Claudia, MD, et al., "Elimination of the Left Atrial Appendage To Prevent Stroke or Embolism ?: Anatomic, Physiologic, and Pathophysiologic Considerations", Chest, Dec. 2003, vol. 124, No. 6, pp. 2356-2362.
Al-Saady, N. M., et al., "Left atrial appendage: structure, function, and role in thromboembolism", Heart, 1999, vol. 82, pp. 547-554.
Sievert, Horst, et al., "Percutaneous Left Atrial Appendage Transcatheter Occlusion to Prevent Stroke in High-Risk Patients With Atrial Fibrillation: Early Clinical Experience", Circulation J.A. M.A., Apr. 23, 2002, pp. 1887-1889.
Coffin, Laurence H., Md, et al., "Use of the Surgical Stapler to Obliterate The Left Atrial Appendage", Surgery, Gynecology & Obstetrics, Jun. 1985, vol. 160, No. 6, pp. 565-566.
Landymore, R., Md, et al., "Staple Closure of the Left Atrial Appendage", The Canadian Journal of Surgery, Mar. 1984, vol. 27, No. 2, pp. 144-145.
Disesa, Verdi J. Md, et al., "Ligation of the Left Atrial Appendage Using an Automated Surgical Stapler", The Annals of Thoracic Surgery, 1988, vol. 46, pp. 652-653.
Japanese Foreign Office Action dated May 10, 2016, issued in corresponding JP Application No. 2015-116009 filed Jun. 8, 2015 (10 pages with English Translation).
EPO Office Action, dated Sep. 9, 2016 in EP Patent Application No. 07761828.8.
Office Action issued in EP Application No. 07761828.8, dated Apr. 15, 2015.
Office Action dated May 18, 2015 for corresponding U.S. Appl. No. 14/047,832 (8 pages).
Final Office Action dated Nov. 30, 2015 during the prosecution of U.S. Appl. No. 14/047,832, 6 pages.
International Preliminary Report on Patentability issued in International Application No. PCT/US2007/068147, issued Nov. 4, 2008.
International Search Report and Written Opinion issued in International Application No. PCT/US2019/024341, dated Jun. 13, 2019.
Kamohara, Keiji et al., A novel device for left atrial appendage exclusion, The Journal of Thoracic and Cardiovascular Surgery, Dec. 2005, 1639-1644, vol. 130, No. 6.
Office Action issued in U.S. Appl. No. 14/177,027, dated Sep. 30, 2016.
International Search Report and Written Opinion dated Feb. 24, 2015, in corresponding International Patent Application PCT/US2014/066438 filed on Nov. 19, 2014 (13 pages).
Office Action issued in U.S. Appl. No. 15/037,963, dated Oct. 18, 2018.
Extended European Search Report issued in EP Application No. 10808715.6, dated Mar. 24, 2015.
Office Action issued in CN Application No. 201080042063.3, dated Apr. 9, 2015.
Office Action issued in CN Application No. 201080042063.3, mailed Nov. 15, 2014.
Final Official Action issued in JP Application No. 2012-524852, mailed Feb. 6, 2015.
Official Action issued in JP Application No. 2015-116009, mailed Dec. 16, 2016.
Official Action issued in JP Application No. 2017-049531, mailed Dec. 15, 2017.
Office Action issued in U.S. Appl. No. 15/165,546, mailed Aug. 30, 2018.
Office Action issued in CN Application No. 201080042063.3, mailed Mar. 20, 2014.
Official Action issued in JP Application No. 2012-524852, mailed Apr. 1, 2014.

(56) References Cited

OTHER PUBLICATIONS

International Preliminary Report on Patentability issued in International Application No. PCT/US2010/045216, issued Feb. 14, 2012.
Final Office Action issued in U.S. Appl. No. 14/177,027, mailed Apr. 5, 2017.
Office Action issued in U.S. Appl. No. 14/177,027, mailed Nov. 16, 2017.
Restriction Requirement issued on Aug. 1, 2018 for U.S. Appl. No. 15/037,963, 7 pages.
Notice of Reason for Refusal issued in JP Application No. 2018-047740, issued Oct. 4, 2018.
Notice of Reason for Refusal issued in JP Application No. 2009-510075, issued Feb. 21, 2012.
Notice of Allowance issued in U.S. Appl. No. 12/168,216, issued Aug. 22, 2011.
Partial European Search Report issued in EP Application No. 08170539.4, issued Mar. 26, 2012.
Extended European Search Report issued in EP Application No. 08170539.4, issued Jul. 11, 2012.
Search Report issued in JP Application No. 2008-317561, issued Feb. 18, 2013.
Notice of Reasons of Refusal issued in JP Application No. 2008-317561, issued Mar. 5, 2013.
Decision of Refusal issued in JP Application No. 2008-317561, issued Jan. 7, 2014.
Reconsideration Report by Examiner Before Appeal issued in JP Application No. 2008-317561, issued Jul. 3, 2014.
Notification of Reason for Refusal issued in KR Application No. 20080000430, issued Oct. 30, 2013.
Notice of Final Rejection issued in KR Application No. 20080000430, issued Apr. 11, 2014.
Written Decision on Registration issued in KR Application No. 20080000430, issued Jul. 28, 2014.
Extended European Search Report issued in EP Application No. 07761828, issued Feb. 3, 2014.
International Preliminary Report on Patentability issued in International Application No. PCT/US2019/024341, dated Oct. 8, 2020.
Non-Final Office Action issued in U.S. Appl. No. 16/366,738 on Aug. 3, 2021, 20 pages.
Non-Final Office Action issued in U.S. Appl. No. 16/821,608 on Oct. 28, 2021, 10 pages.
Extended Search Report issued in European Patent Application No. 19777210.6 on Nov. 11, 2021, 7 pages.
Advisory Acion issued in U.S. Appl. No. 16/366,738 on Aug. 6, 2022, 8 pages.
Japanese Office Action issued in Japan Patent Application No. JP2020-551904 dated Feb. 21, 2023 (4 pages).

\* cited by examiner

FASTENER APPLICATOR WITH INTERLOCK

RELATED APPLICATIONS

This application is a continuation of U.S. patent application Ser. No. 16/599,779, filed Oct. 11, 2019, which is a divisional of U.S. patent application Ser. No. 15/037,963, filed May 19, 2016, now U.S. Pat. No. 10,485,545, which is a national phase application of International Patent Application PCT/US2014/066438, filed Nov. 19, 2014, which claims the benefit of priority to provisional U.S. Patent Application Ser. No. 61/906,290 filed Nov. 19, 2013. The disclosures of U.S. patent application Ser. No. 16/599,779, U.S. patent application Ser. No. 15/037,963, International Patent Application PCT/US2014/066438, and provisional U.S. Patent Application Ser. No. 61/906,290 are hereby incorporated by reference in their entireties.

FIELD OF THE DISCLOSURE

The present disclosure pertains broadly to the field of fasteners and/or applicators. More specifically, the disclosure relates to surgical applicators of implants and/or fasteners, including but not limited to sterilized fasteners such as staples.

BACKGROUND

Atrial fibrillation is a relatively common condition characterized by a very rapid heartbeat of the left and right atrium. While atrial fibrillation is not normally fatal itself, it has been associated with an increased risk of stroke. It is believed that the rapid heartbeat causes blood to pool in the left atrial appendage which causes emboli that are released into the left atrium from where they can enter the cerebral vasculature, thus causing a stroke. In addition to stroke, the emboli can enter coronary circulation, potentially causing myocardial infarction, or can enter peripheral circulation, potentially causing peripheral vascular disease.

The risk of stroke in patients suffering from atrial fibrillation can be reduced in a variety of ways. For example, blood thinning drugs can be used to reduce the risk of clot formation. The use of blood thinners, however, is contraindicated in patients at risk of bleeding disorders. More aggressive treatment protocols have been proposed which involve closing the left atrial appendage. Closure and excision may be performed in open surgical procedures, typically requiring the patient to be placed on bypass and the chest to be opened through the sternum. Alternatively, thoracoscopic and other less invasive procedures have been proposed. U.S. Pat. No. 5,306,234 teaches the performance of heating heart procedures using otherwise conventional surgical techniques. The use of conventional techniques through small chest penetrations while the heart is beating can be difficult to perform. U.S. Pat. No. 5,865,791 describes an intravascular approach where tools are introduced through the vasculature and passed into the left atrium. The tools are used to ablate or fuse the left atrial appendage from the inside using energy, adhesives, or the like. The '791 patent also describes a thoracoscopic procedure where a tether is placed over the neck of the atrial appendage and tied off to achieve isolation. The '791 patent still further suggests other closure elements including sutures, staples, shape-memory wires, biocompatible adhesives, and the like. U.S. Pat. No. 6,488,689 describes a transpericardial procedure where the distal tip of the left atrial appendage is grasped and pulled backwardly through a capture loop which encircles the base of the left atrial appendage.

A compliant closure structure for the sealing bodily structures such as the left atrial appendage is described in co-pending, commonly owned U.S. Patent Publication 2007/17260278 (application Ser. No. 11/744,135), the full disclosure of which is incorporated herein by reference in its entirety. The compliant structure described in the '278 publication comprises an elastomeric body having a pair of opposed legs which may be arranged in an oval or a U-shaped configuration to define an opening therebetween. By placing the opening between the legs over the left atrial appendage and aligning it with the base of the appendage, the structure may be closed to provide the desired sealing. To hold the structure closed, a number of discrete, axially spaced-apart tissue penetrating fasteners are arranged along the lengths of each of the legs. By compressing the legs together to press-lit the closure devices, the compliant structure may be closed to provide a compliant seal which effectively isolates the left atrial appendage.

The '278 publication describes a particular delivery tool for the compliant closure structure. The delivery tool includes jaws which can be inserted into the legs of the closure structure and actuated to close the jaws in the legs over the left atrial appendage. The jaws further include comb studs which engage and press fit the closure devices in order to hold the compliant structure in its closed, sealing configuration. The studs are intended to be retracted to allow the delivery tool to be removed.

Although functional, the delivery tool of the '278 publication has certain shortcomings. For example, the actuation of the jaws and retraction of the comb studs can be performed out of order, increasing the risk that the delivery of the compliant structure will fail. Moreover, positioning and orientation of the delivery tool can be difficult, particularly when the tool is introduced through an intercostal penetration to access the left atrium. Additionally, the jaws in the device of the '278 publication are attached in the axial plane of the device shall. Such a straight line of attachment can make it more difficult to align the jaws with the base of the appendage and across the os (i.e., ostium) of the atrium leading into the appendage. If the closure device is not aligned across the base to completely close the os, gaps or openings (referred to as "cul-de-sacs") can remain at the site of closure, increasing the risk of thrombus formation in the atrium. The importance of forming a complete seal of the os which is free from such cul-de-sacs is discussed in Sulzberg et al. (2008) Eur. J. Cardiothoracic Surg. 34:766-770.

For these reasons, it would be desirable to provide improved delivery tools for use with the tissue closure devices described in U.S. Patent Publication 2007/0260278. It would be further desirable if the delivery tools and methods of their use were compatible with the delivery of other tissue closure devices and for procedures in addition to closure of the left atrial appendage.

SUMMARY

A surgical applicator for a fastener according to an example embodiment comprises a handle, a first trigger coupled movably with respect to the handle, and a second trigger coupled movably with respect to the first trigger, hut operatively arranged to move in tandem with the first trigger during movement of the first trigger. An interlock is coupled to the second trigger and operatively arranged to selectively prevent movement of the second trigger relative to the first trigger depending on a position of the first trigger with respect to the handle.

According to an example embodiment, the interlock permits movement of the second trigger relative to the first trigger when the first trigger is moved from a first position to a second position, and restricts movement of the second trigger relative to the first trigger when the first trigger is not in the second position.

According to an example embodiment, a second interlock is coupled to the first trigger and operatively arranged to selectively prevent movement of the first trigger relative to the handle depending on a position of second trigger.

According to an example embodiment, a jaw assembly is selectively opened and closed via movement of the first trigger.

According to an example embodiment, movement of the second trigger selectively retracts one or more fastener supporting structures of the jaw assembly with respect to at least one jaw of the jaw assembly.

According to an example embodiment, the interlock includes a cam follower engaged with a cam channel.

According to an example embodiment, the handle includes the cam channel and the second trigger includes the cam follower.

According to an example embodiment, the cam channel has a first leg that permits tandem movement of the second trigger with the first trigger during closing of the first trigger and a shoulder that prevents movement of the second trigger relative to the first trigger until the first trigger is closed.

According to an example embodiment, the cam channel has a second leg that permits tandem movement of the second trigger with the first trigger during re-opening of the first trigger after the second trigger has been closed relative to the first trigger.

According to an example embodiment, the cam channel includes at least one leg formed concentrically with respect to a first pivot about which the first trigger is rotatably coupled to the handle and a transverse portion funned concentrically with respect to a second pivot about which the second trigger is rotatably coupled to the first trigger.

According to an example embodiment, the at least one leg includes two legs, and the transverse portion is connected between the two legs.

A fastener applicator according to an example embodiment comprises a handle, a first trigger coupled rotatably with respect to the handle, and a second trigger coupled rotatably with respect to the handle. An interlock is disposed with the second trigger and comprises a cam follower engaged in a cam channel that selectively prevents rotation of the second trigger relative to the first trigger depending on a location of the cam follower within the cam channel. The location of the cam follower in the cam channel is set by a position of the first trigger.

According to an example embodiment, the handle includes the cam channel and the second trigger includes the cam follower.

According to an example embodiment, the cam channel has at first leg that permits tandem movement of the second trigger with the first trigger during closing of the first trigger and a shoulder that prevents movement of the second trigger relative to the first trigger until the first trigger is closed.

According to an example embodiment, the cam channel has a second leg that permits tandem movement of the second trigger with the first trigger during re-opening of the first trigger after the so and trigger has been closed relative to the first trigger.

A fastener applicator according to an example embodiment comprises a handle, a shaft extending distally from the handle and a jaw assembly at a distal end of the shaft having one or more fastener supporting structures. A first trigger is coupled movably with respect to the handle and to the jaw assembly such that movement of the first trigger relative to the handle selectively closes the jaw assembly. A second trigger is coupled movably with respect to the first trigger, the second trigger coupled to the jaw assembly such that movement of the second trigger relative to the first trigger selectively retracts die one or more fastener supporting structures; and an interlock coupled to the second trigger and operatively arranged to selectively prevent movement of the second trigger relative to the first trigger depending on a position of the first trigger.

According to an example embodiment, the interlock permits movement of the second trigger relative to the first trigger when the first trigger is closed and prevents movement of the second trigger relative to the first trigger when the first trigger is open.

According to an example embodiment, a second interlock is coupled to the first trigger and operatively arranged to selectively prevent movement of the first trigger relative to the handle depending on a position of second trigger.

According to an example embodiment, the interlock includes a cam follower engaged with a cam channel.

According to an example embodiment, the handle includes the cam channel and the second trigger includes the cam follower.

According to an example embodiment, the second trigger is movable in tandem with the first trigger during movement of the first trigger.

A fastener applicator according to an example embodiment comprises a handle, a first trigger movable with respect to the handle between a first position and a second position, and a second trigger movable with respect to the first trigger between an initial position and an actuated position. A first interlock is coupled to the second trigger and operatively arranged to selectively prevent movement of the second trigger relative to the first trigger until the first trigger is moved into the second position. A second interlock is coupled to the first trigger and operatively unarmed to selectively prevent movement of the first trigger relative to the handle until the second trigger is moved into the actuated position.

According to an example embodiment, a pair of jaws is included, with the first trigger coupled to the pair of jaws for setting the pair of jaws in an open configuration when the first trigger is in the first position and in a closed configuration when the first trigger is in the second position.

According to an example embodiment, one or more fastener supporting structures are disposed with the pair of jaws. The second trigger is coupled to the one or more fastener supporting structures for setting the one or more fastener supporting structures in a deployed configuration when the second trigger is in the initial position and in a retracted configuration when the second trigger is in the actuated position.

A method of operating a fastener applicator according to an example embodiment comprises: (i) repositioning a first trigger of the fastener applicator with respect to a handle from a first position to a second position, (ii) moving a second trigger in tandem with the first trigger, (iii) preventing repositioning of a second trigger between an initial position and an actuated position relative to the first trigger with an interlock coupled to the second trigger until the first trigger is moved to the second position, and (iv) repositioning the second trigger to the actuated position relative to the first trigger after the first trigger is moved to the second position.

A method of operating a fastener applicator according to an example embodiment comprises: (i) moving a first trigger of the fastener applicator with respect to a handle from a first position to a second position, (ii) preventing movement of a second trigger between an initial position and an actuated position relative to the first trigger with an interlock coupled to the second trigger until the first trigger is moved to the second position, (iii) rearranging a cam follower and a carp channel of the interlock with respect to each other due to the moving of the first trigger to the second position, and (iv) moving the second trigger to the actuated position relative to the first trigger after the first trigger is moved to the second position.

A method of operating a fastener applicator according to an example embodiment comprises: (i) moving a first trigger of the fastener applicator with respect to a handle from a first position to a second position, (ii) preventing movement of a second trigger between an initial position and an actuated position relative to the first trigger with a first interlock coupled to the second trigger until the first trigger is moved to the second position, (iii) moving the second trigger to the actuated position relative to the first trigger after the first trigger is moved to the second position, (iv) preventing movement of the first trigger relative to the handle hack to the first position with a second interlock coupled to the first trigger until the second trigger is moved to the actuated position, and (v) moving the first trigger hack to the first position relative to the handle after the second trigger is moved to they actuated position.

A method of operating a fastener applicator according to an example embodiment comprises: (i) repositioning a first trigger of the fastener applicator with respect to a handle from a first position to a second position, (ii) closing a jaw assembly coupled to the handle of the fastener applicator due to movement of the first trigger to the second position, (iii) preventing repositioning of a second trigger between an initial position and an actuated position relative to the first trigger with an interlock coupled to the second trigger until the first trigger is moved to the second position, (iv) repositioning the second trigger to the actuated position relative to the first trigger after the first trigger is moved to the second position, and (v) retracting one or more fastener supporting structures comprising at least one protrusion movably extendable and retractable with respect to at least one jaw of they jaw assembly of the fastener applicator due to repositioning of the second trigger to the actuated position.

According to an example embodiment, the fastener applicator comprises a second interlock coupled to the first trigger and the method further comprises preventing movement of the first trigger from the second position to the first position with the second interlock until the second trigger is moved to the actuated position relative to the first trigger, and repositioning the first trigger from the second position back to the first position after the second trigger is moved to the actuated position relative to the first trigger.

According to an example embodiment, the interlock includes a cam follower engaged with a cam channel.

According to an example embodiment, rotating the first trigger front the first position to the second position includes traversing the cam follower along a first leg of the channel.

According to an example embodiment, the first leg is formed concentrically with respect to a pivot about which the first trigger rotates.

According to an example embodiment, rotating the second trigger to the actuated position relative to the first trigger includes traversing the cam follower along a portion of the channel transverse to the first leg.

According to an example embodiment, the handle includes the cam channel and the second trigger includes the cam follower.

According to an example embodiment, rotating the first trigger from the first position to the second position including moving the second trigger in tandem with the first trigger.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Embodiments of the present disclosure provide alternative and improved apparatuses, systems, and methods for deploying one or more closure devices or fasteners to tissue. An exemplary tissue structure of a patient at risk of stroke or other adverse events resulting from emboli released into circulation from the left atrial appendage, may include the left atrial appendage. Patients benefiting front the exemplary procedures disclosed herein will at least partially include those suffering from atrial fibrillation which can cause clot and thrombus formation in the left atrial appendage, thus increasing the chance of emboli release.

Exemplary embodiments of the present disclosure provide a mechanical closure device applicator for introducing the fastener over the tissue structure, which fastener is left in place in order to close and/or seal the tissue structure. A portion of the tissue structure extending beyond the fastener may then be cut, excised, or otherwise removed, although this may be left to the physician's preference. In one embodiment, the tissue fastener comprises a compression body having at least two opposed, compliant tissue-engaging surfaces which are placed over opposite sides of the tissue structure. In this embodiment, the tissue-engaging surfaces are held together by a plurality of axially spaced-apart tissue-penetrating fasteners, which extend from one of the surfaces, through the intermediate tissue, and into the other surface to both hold the compression body in place and to apply a desired level of compression force, which is determined by both the softness of the compression body and the distance between the surfaces when they are fully attached. A well may be provided in the compression body around the tissue-penetrating barb of the fastener such that a gasket seal is formed by the compression body around the puncture site in the tissue. A stabilizing lip may be provided in one leg of the compression body to prevent a rolling motion of one leg with respect to another leg of the compression body in order to keep the two opposing soft members linearly aligned. More detailed descriptions of fasteners suitable for use with embodiments of the present disclosure are found in patent publication U.S. 2007/0260278, the full disclosure of which has been previously incorporated herein by reference.

Figure 1:
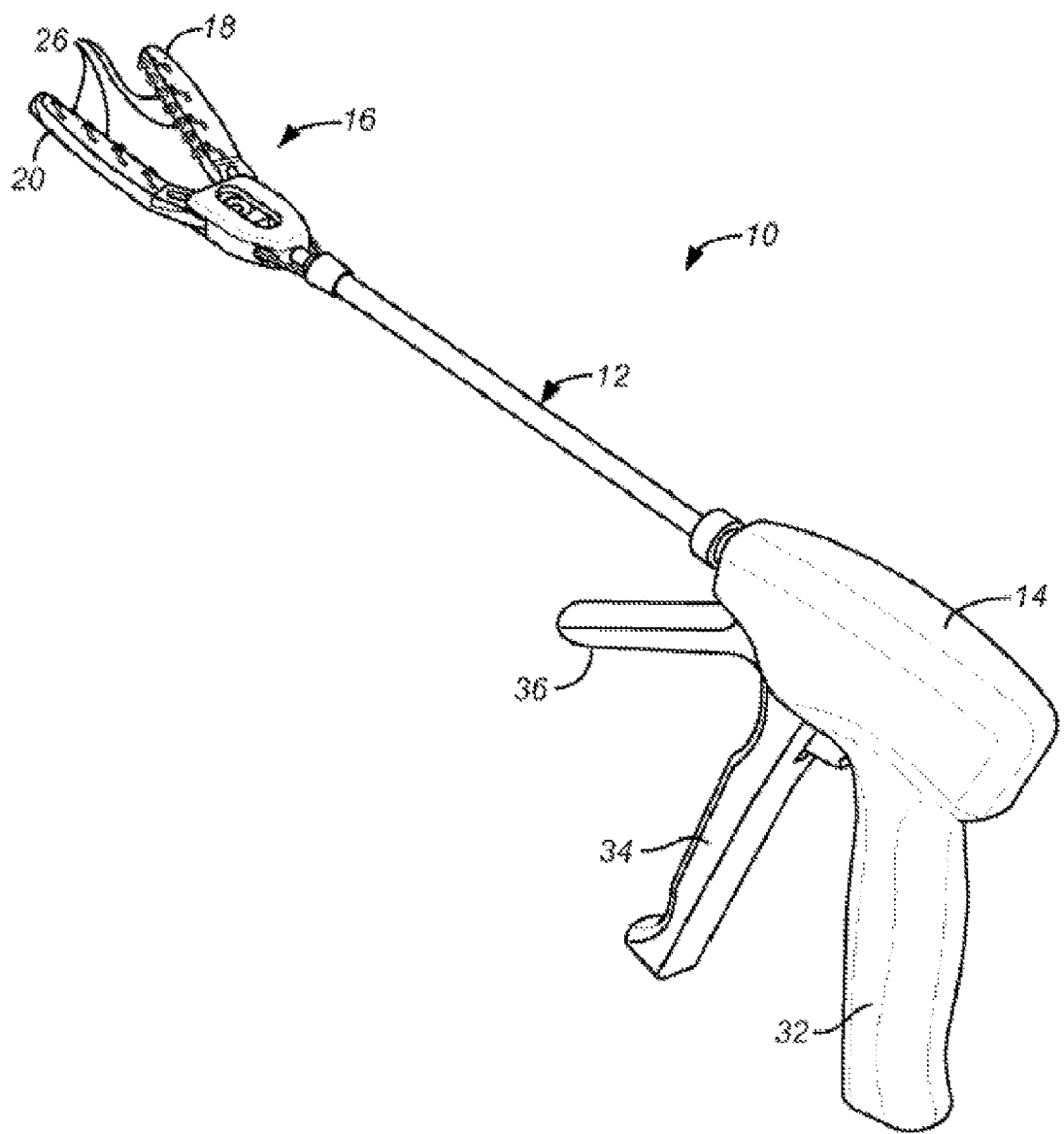
FIG. 1 is a perspective view of a closure device applicator constructed in accordance with to an example embodiment of the present disclosure.
Figure 2:
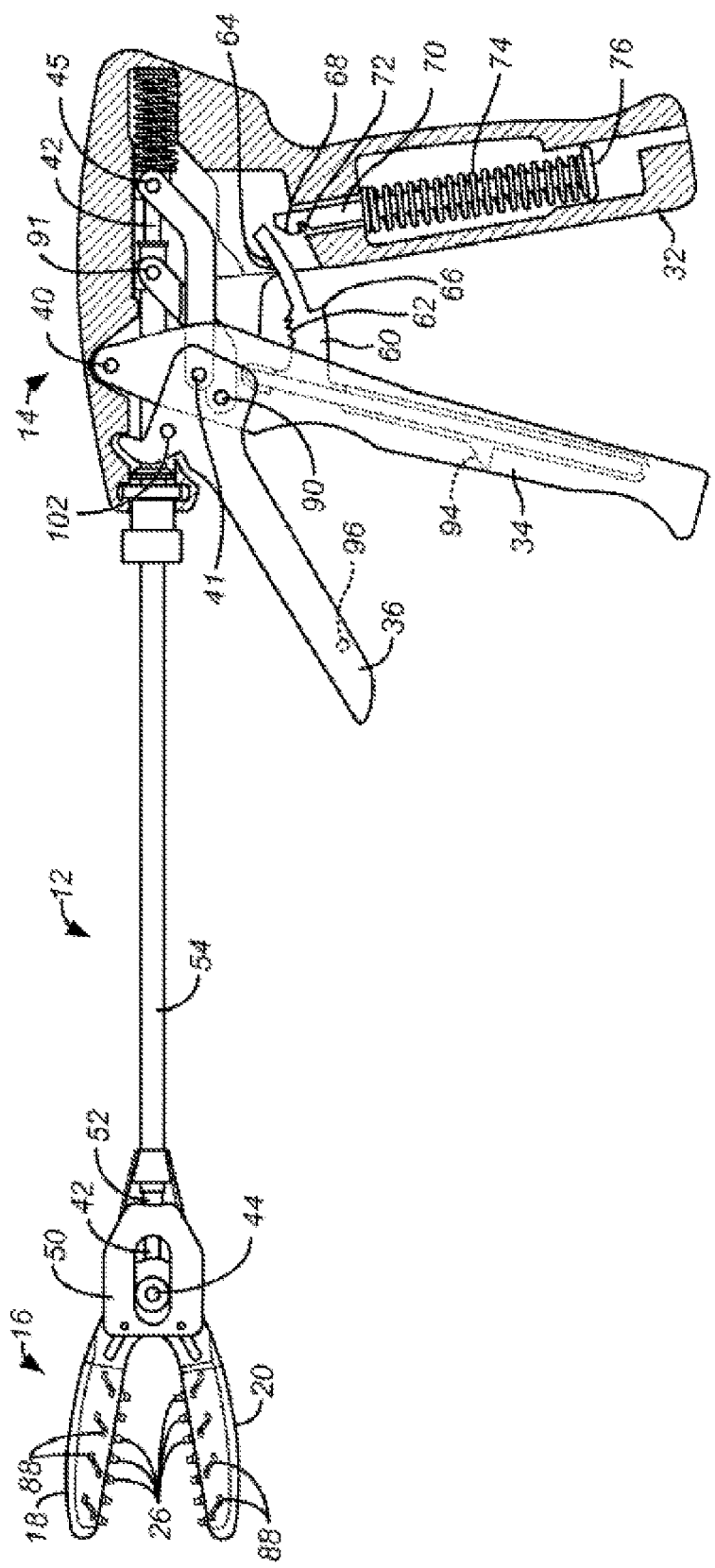
FIG. 2 is a partial cross-sectional elevation view of the closure device applicator of FIG. 1, shown with the jaws open and rotated 90° relative to the position shown in FIG. 1.
Figure 6A:
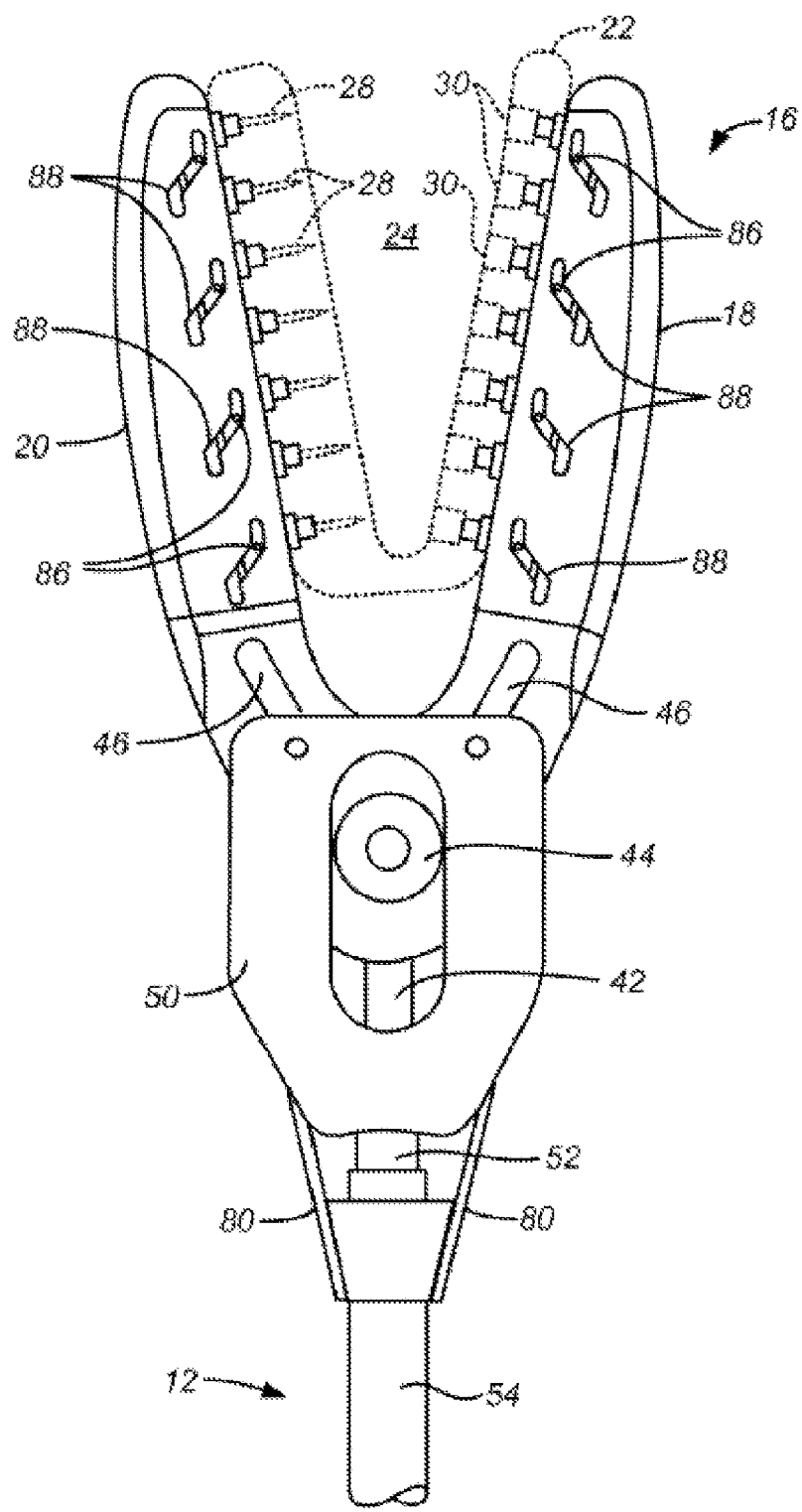
FIG. 6A-6D illustrate the movement of the jaw and stud engagement with the closure devices of a tissue closure device according to an example embodiment of the present disclosure.

Referring now to FIG. 1, a fastener applicator 10 constructed in accordance with various embodiments of the present disclosure comprises a shaft 12 having a handle assembly 14 at its proximal end, and a jaw assembly 16 at a distal end, when individual jaws 18 and 20 are adapted to carry a fastener 22, as best illustrated in FIGS. 6A-6D. The fastener 22 is shown in an example embodiment to have a U-shaped configuration which defines a V-shaped region 24 for receiving the left atrial appendage or other tissue structure when the jaws are open as shown in FIGS. 1, 2, and 6A. A plurality of studs 26 are formed along the inner surfaces of each jaw 20 and 18 to engage tissue-penetrating fasteners which comprise penetrating components 28 and receptacle components 30, as best shown in FIG. 6A. The handle assembly 14 will include a handle 32, a first trigger 34, and a second trigger 36.

Figure 10:
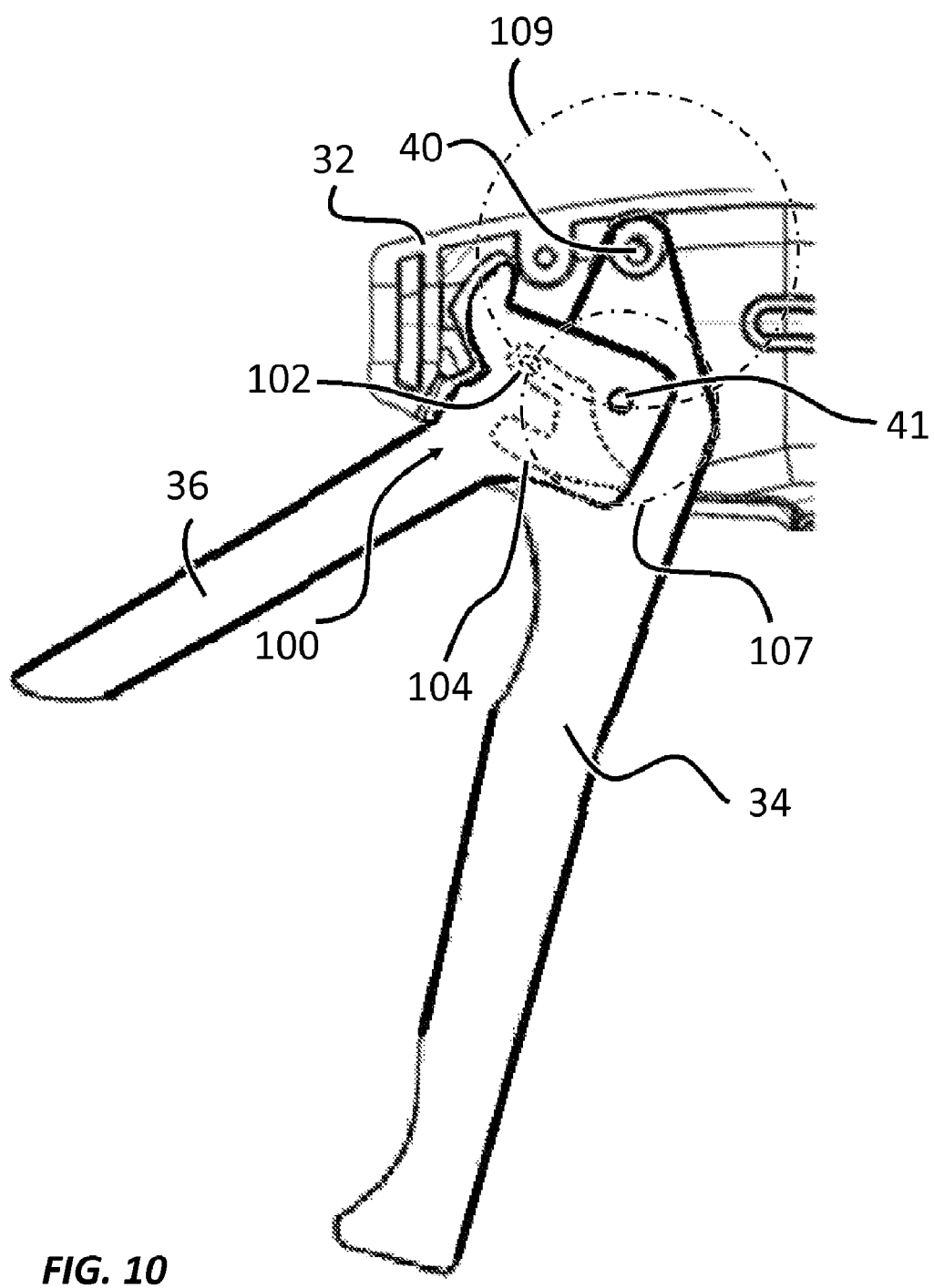
FIG. 10 illustrates operation of the interlock of FIG. 8 with respect to the first and second triggers of the applicator of FIG. 1.

Referring now to FIGS. 2 and 6A, the fastener applicator 10 is shown in its shelf or delivery configuration with the fastener 22 received over the jaw assembly 16 and the V-shaped opening 24 in the device ready to be placed over a tissue structure such as the left atrial appendage (see FIG. 10). The triggers 34 and 36 are each respectively movable between an initial or first position and an actuated or second position. As will be discussed in more, detail below, the first trigger 34 is movable between its respective positions relative to the handle 32, while the second trigger 36 is movable between its respective positions relative to the first trigger 34. In one embodiment, in their respective first positions, the first trigger 34 and the second trigger 36 are initially in a fully open position, that is, pivoted fully away from the handle 32. For this reason, it is to be understood that any mention of "opening" the first trigger 34 refers more generally to moving the first trigger 34 toward its first or initial position, white any mention of "closing" the first trigger 34 or the second trigger 36 refers more generally to moving the first trigger 34 or the second trigger 36 towards its respective second or actuated position.

Figure 3:
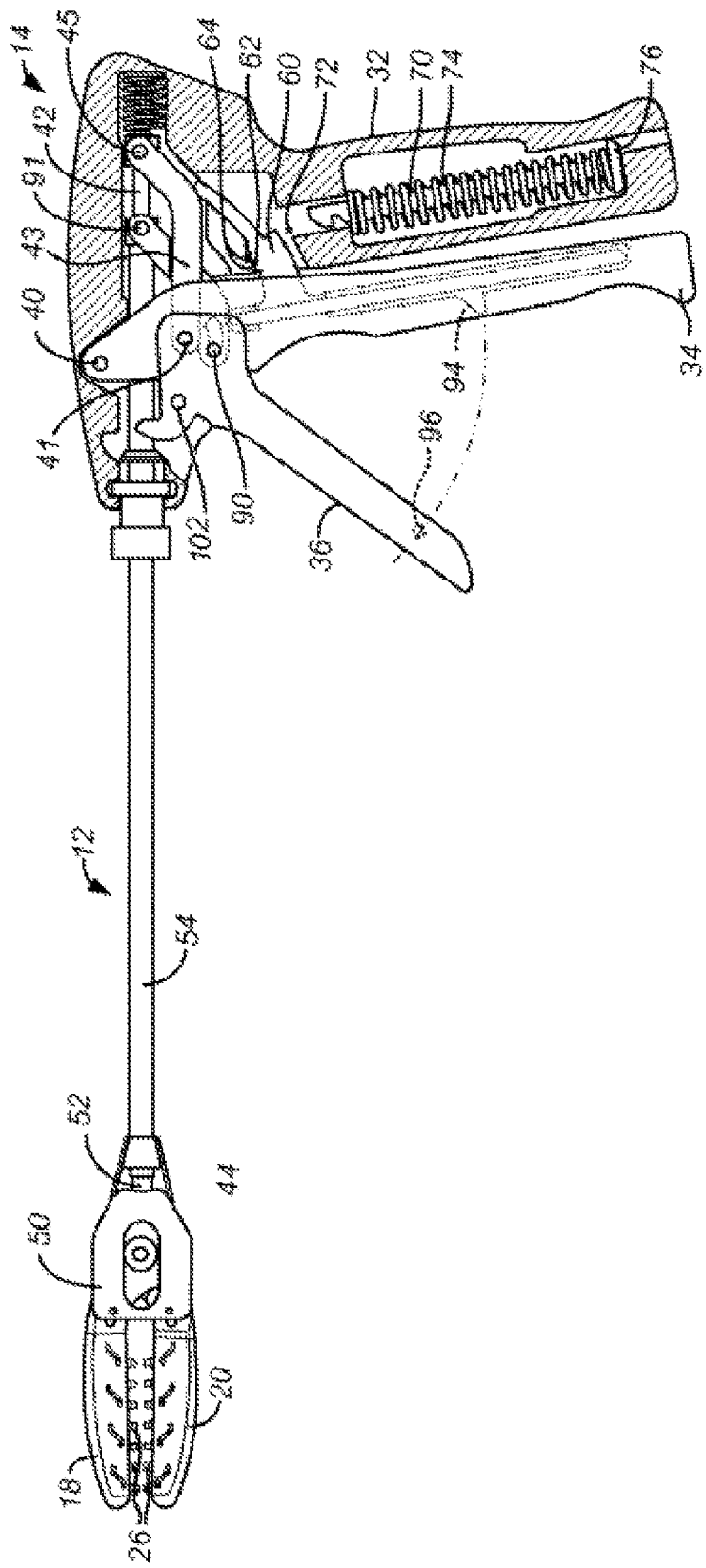
FIG. 3 is a partial, cross-sectional elevation view of the device applicator similar to FIG. 2, shown with the first trigger closed relative to the handle in order to close the jaws, and the second trigger open (or spaced apart) with respect to the first trigger.
Figure 6B:
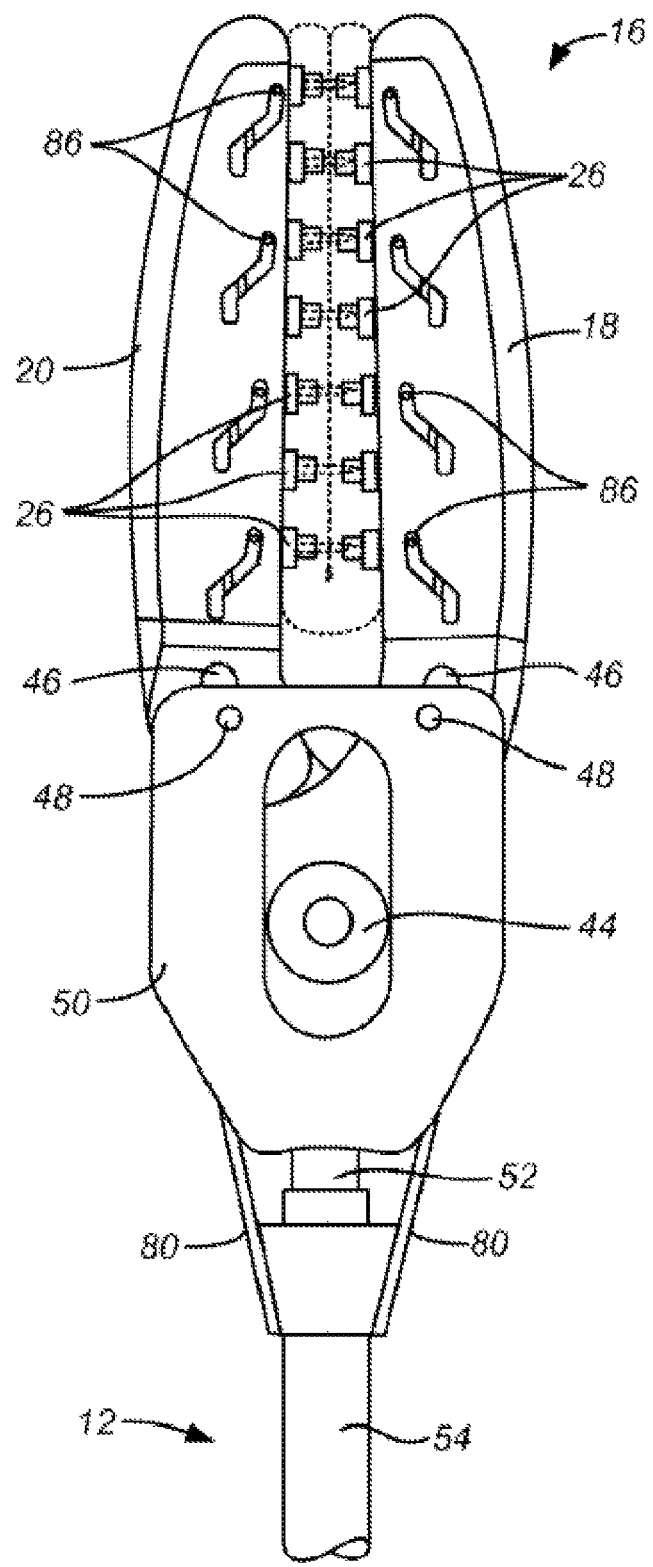

After the fastener 22 is advanced over the left atrial appendage or other target tissue structure, the jaws 18 and 20 are closed by manually pulling the first trigger 34 toward the handle 32, as shown in FIGS. 3 and 6B. The first trigger 34 is mounted on a pin or pivot 40, which is shown to be fixedly secured to the handle assembly 14, thereby rotatably coupling the first trigger 34 to the handle 32. Closing the first trigger 34 with respect to the handle 32, that is, pivoting about the pivot 40 from the first position of the first trigger 34 to the second position, proximally retracts the rod 42 which is linked to the first trigger 34 by a pin or pivot 41 and a lever 43. The rod 42 is attached to a pin 44 (FIG. 6B) which is pivotally attached to the proximal ends of the jaws 18 and 20 and proximally retracts the jaws so that they are closed by the movement of slots 46 over pins 48 in an end frame 50 attached to a stationary sleeve 52. When the jaws 18 and 20 are closed, the studs 26 engage the tissue penetrating components 28 and the tissue penetrating receptacles 30 so that they engage and lock with each other, thus closing the two legs of the fastener 22, as shown in FIG. 6B.

The second trigger 36 may be mounted on the pin 41 so that the second trigger 36 moves, actuates, or closes with respect to the handle 32 in tandem with the first trigger 34. In this way, the second trigger 36 is rotatably coupled to the handle 32, although indirectly via the pin 41 and the first trigger 34. By "in tandem" it is meant that movement of the first trigger 34 translates at least partially into corresponding movement of all or portions of the second trigger 36. In the illustrated embodiment, movement of the first trigger 34 causes a substantially equivalent amount of rotational movement of the second trigger 36, although there could be gears, linkages, springs, or the like to cause a lesser or greater degree of movement of the second trigger 36 to result from corresponding movement of the first trigger 34.

The applicator 10 may optionally include an interlock 60 in some embodiments. According to the illustrated embodiment, as the first trigger 34 and the second trigger 36 are moved in tandem, a ratcheting tooth surface 62 of the interlock 60 is closed against pins 64, as shown in FIG. 3, so that the first trigger 34 cannot be ne-opened once the jaw assembly 16 has been closed, either completely or to a certain degree of closure or spacing between the jaws. This is advantageous as described above, since the jaws should not be completely opened prior to retracting the studs 26 by closing the second trigger 36, as will be described below. The ratcheting tooth surface 62 can include any number of ratchets or notches such that the first trigger 34 can be progressively closed (i.e., brought into approximation of the handle 32) by more fully driving the ratcheting tooth surface 62 along the pins 64 in the direction of closure for the first trigger 34 (e.g., from the configuration of FIG. 2 to the configuration of FIG. 3).

Additionally, as the first trigger 34 is moved to its actuated, closed, or second position (i.e., moved or actuated to the configuration of FIG. 3) in order to close the jaws 18 and 20 of the jaw assembly 16, a corner 66 (see FIG. 2) of the interlock 60 will engage an inclined surface 68 on a clicker pin 70 to disengage the clicker pin 70 from a holding pin 72, thus allowing a spring 74 to push the pin 70 downward so that a bottom surface 76 thereof strikes the bottom of the handle 32, thus causing a loud click to audibly alert the physician that the jaws have been closed and the interlock 60 has been engaged. This audible confirmation indicates to the physician or other medical personnel that the fastener 22 has been closed and that the studs 26 can be retracted.

Figure 4:
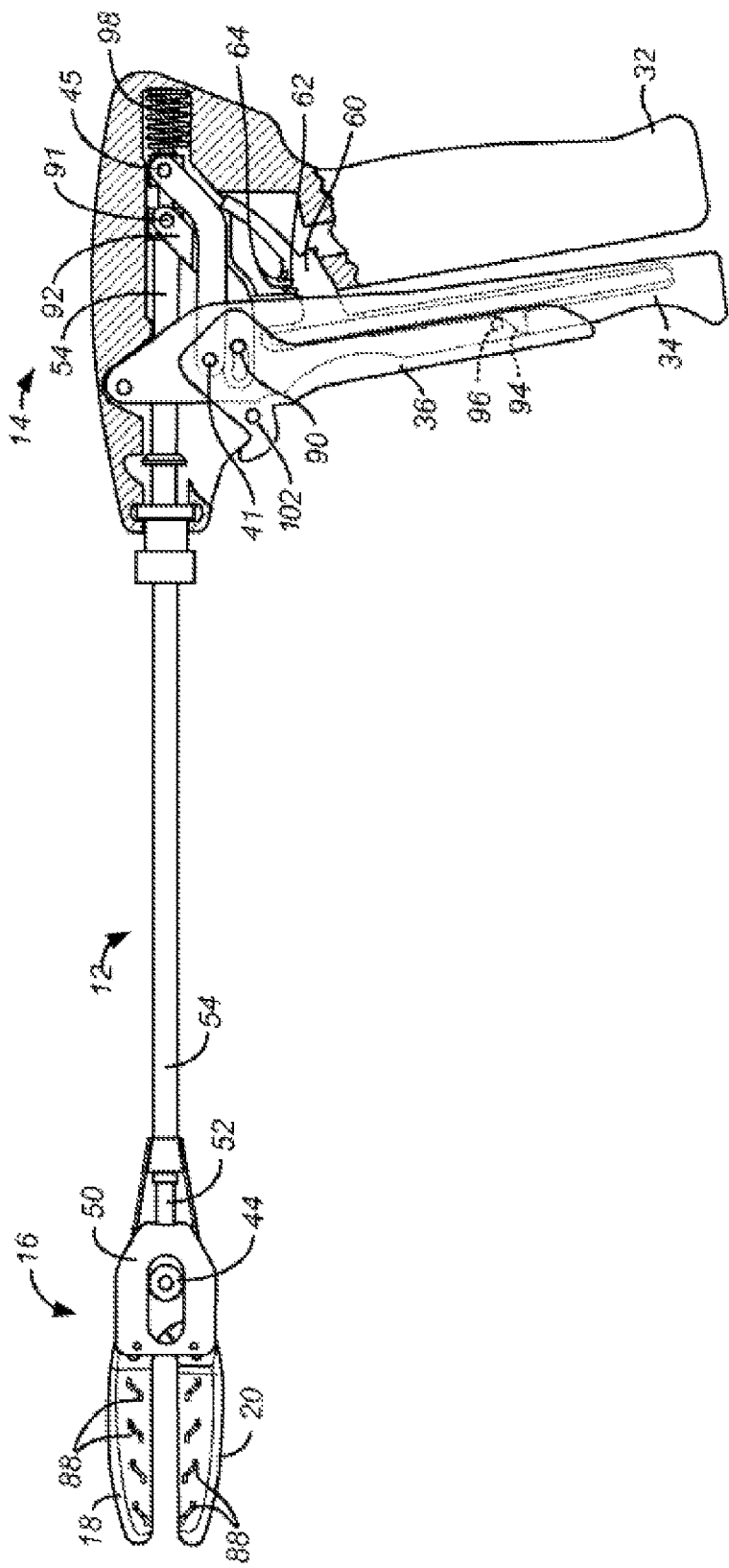
FIG. 4 is a partial, cross-sectional elevation view of the closure device applicator similar to that shown in FIGS. 2 and 3 with the second trigger closed relative to the first trigger demonstrating a retraction of the closure device-engaging studs.
Figure 6C:
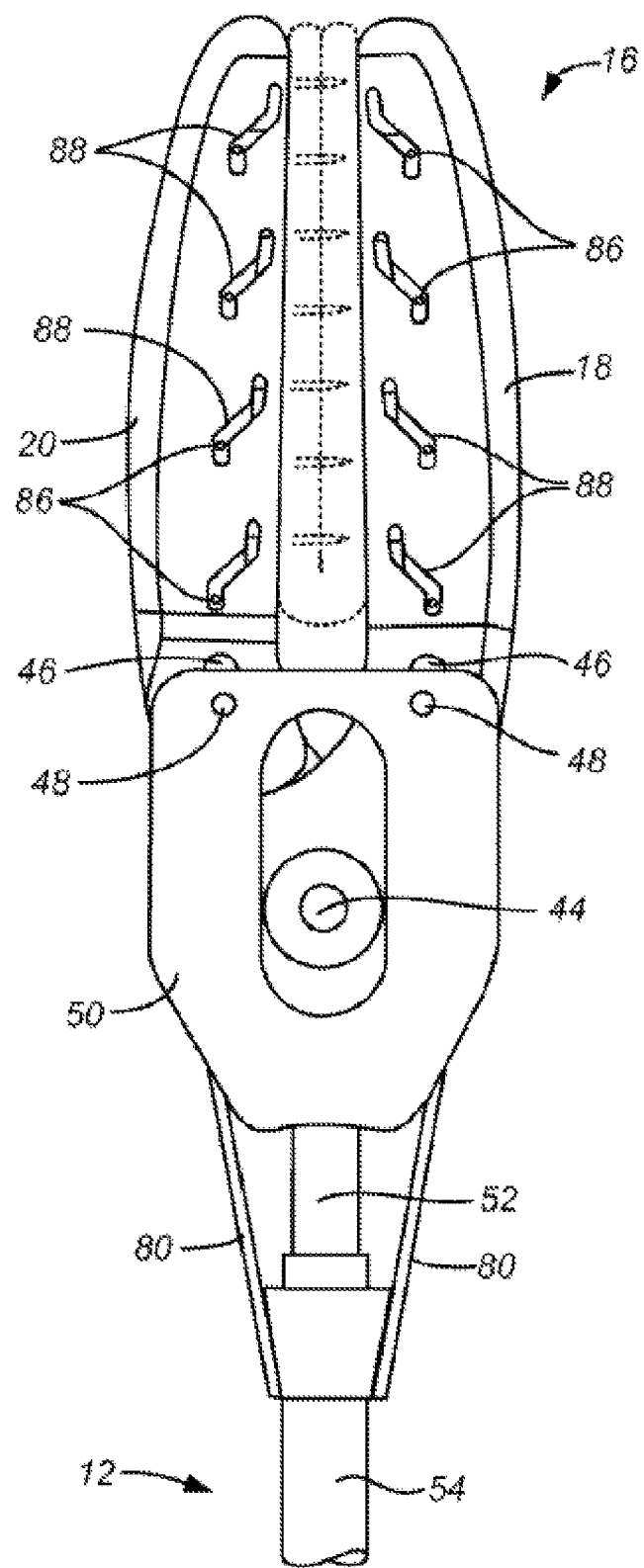
Figure 6D:
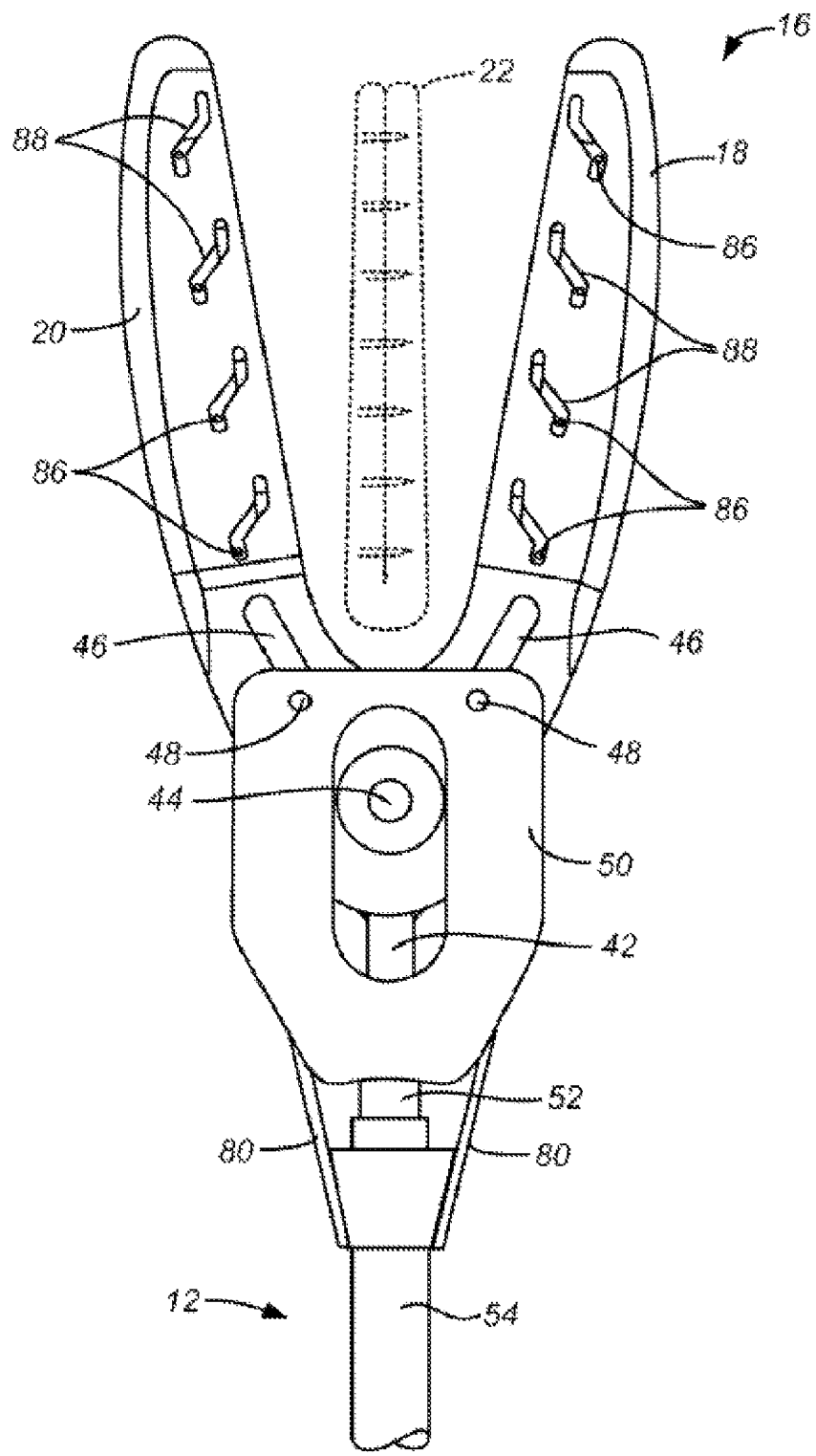
Figure 7:
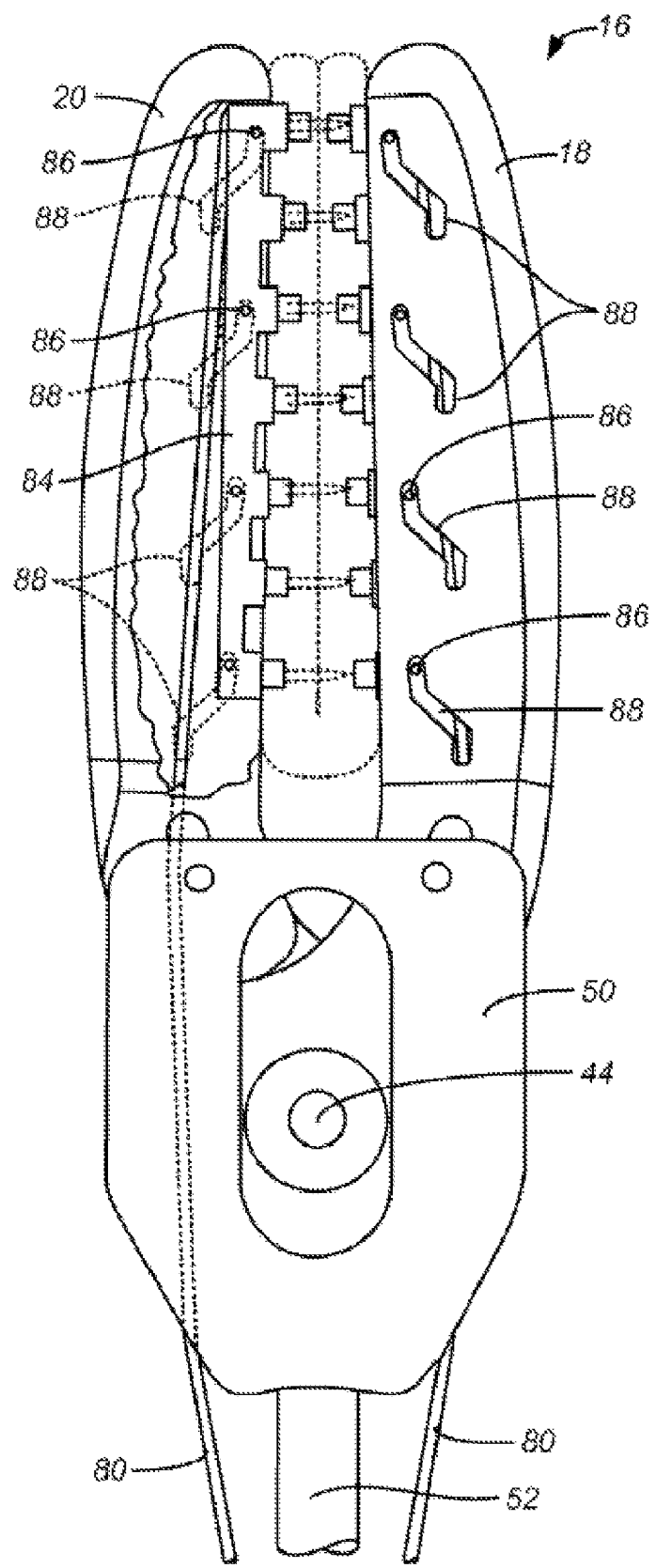
FIG. 7 illustrates an exemplary mechanism by which the closure device-engaging studs are retracted within the jaws according to an example embodiment of the present disclosure.

The studs 26 are initially in an extended configuration, as shown in FIGS. 2-3 and 6A-6B, and then retracted by closing second trigger 36 against the first trigger 34, as shown in FIGS. 4 and 6C. Closure of the second trigger 36 relative to the first trigger 34 draws the outer sleeve 54 proximally over the stationary sleeve 52 which draws pull wires 80 proximally to full stud combs 84 or other fastener supporting structures, proximally, as shown in FIG. 7. The stud combs 84 are mounted on pins 86 which travel in slots 88 formed in each of the jaws 18 and 20. The second trigger 36 is pivotally mounted on, or rotatably coupled to, the first trigger 34 by the pin 41 and is coupled to the stationary sleeve by pins 90 and 91 and a lever 92. It is to be appreciated that the studs 26 can take other shapes or arrangements and/or that other fastener supporting structure (i.e., structures capable of supporting the fasteners 22 during closing and engaging thereof) can be included in lieu of the studs 26 that are either disengaged from or engaged to the fastener 22 upon intentional closure or movement of the second trigger 36. For example, in lieu of a plurality of individual studs 26, a supporting structure in the form of a single unitary rail supporting all of the components 28 can be included in one embodiment.

Figure 5:
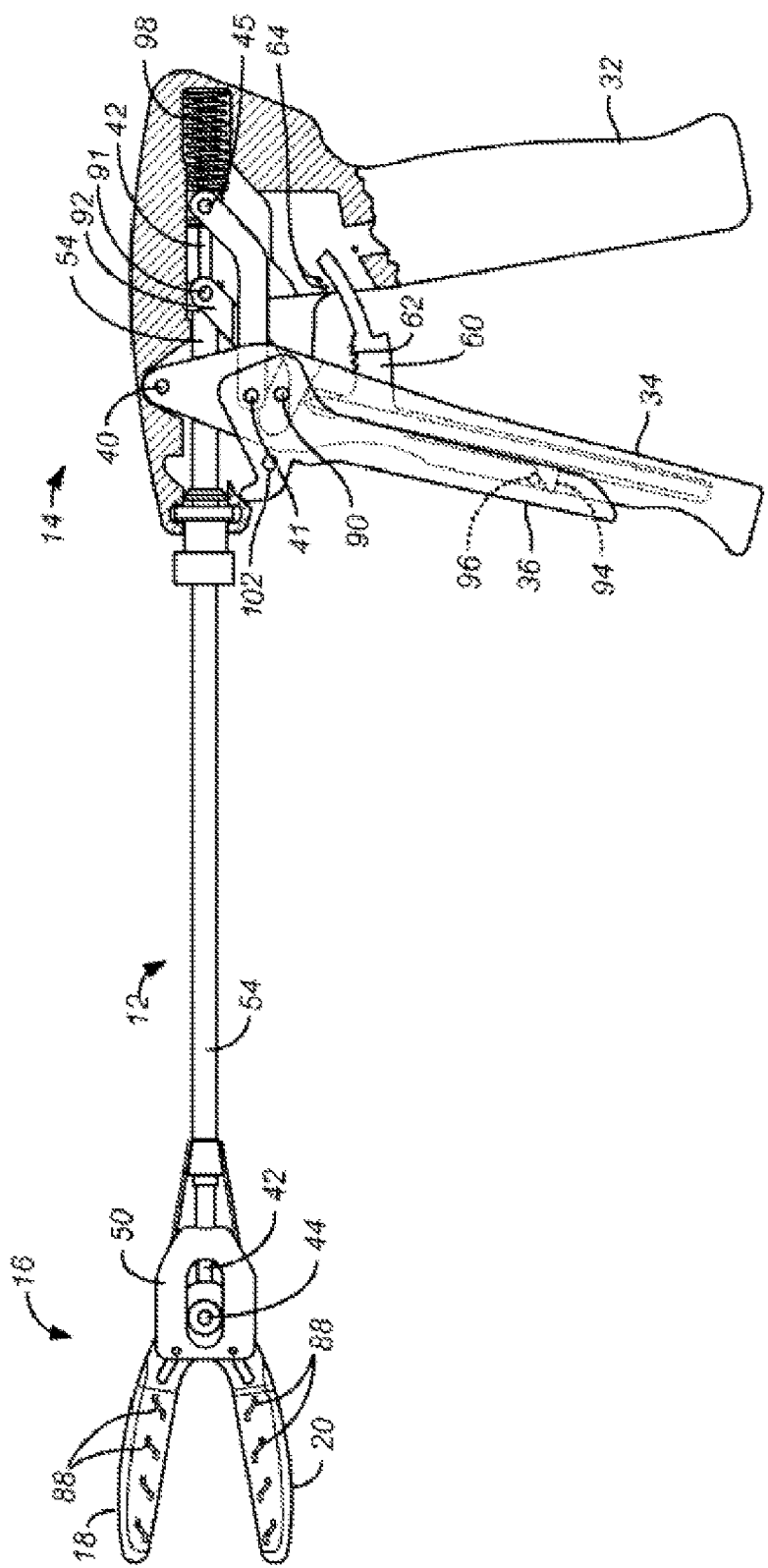
FIG. 5 is a partial, cross-sectional elevation view of the closure device applicator of FIGS. 2-4, shown with the first trigger re-opened with respect to the handle in order to open the jaws while the closure device-engaging studs remain retracted.

Movement of the second trigger 36 relative to the first trigger 34, e.g., closure of the second trigger 36, disengages the interlock 60 by engaging a ramped surface 94 attached to the interlock 60 against a fixed pin 96 in the second trigger 36. In this way, the interlock 60 selectively permits or prevents movement, e.g., opening, of the first trigger 34 depending on a position of the second trigger 36. In other words, movement of the second trigger 36 to its corresponding second position, relative to the first trigger 34, releases the interlock 60. The pin 96 follows the path shown in broken line in FIG. 3 to engage the surface 94. The ramped surface 94 is caused to move downwardly, pulling the ratchet teeth 62 away from the fixed pins 64, as shown in FIGS. 4 and 5. The triggers 34 and 36 are now ready to be opened in order to open the jaws, as will now be described.

Referring now to FIGS. 5 and 7C, the jaws 18 and 20 may be opened by releasing manual compression on the first and second triggers 34 and 36, allowing spring 98 which was compressed during closure of the first trigger 34 to push rod 42 (attached to pivot 44) distally forward, opening the jaws and leaving the fastener 22 in place.

Figure 8:
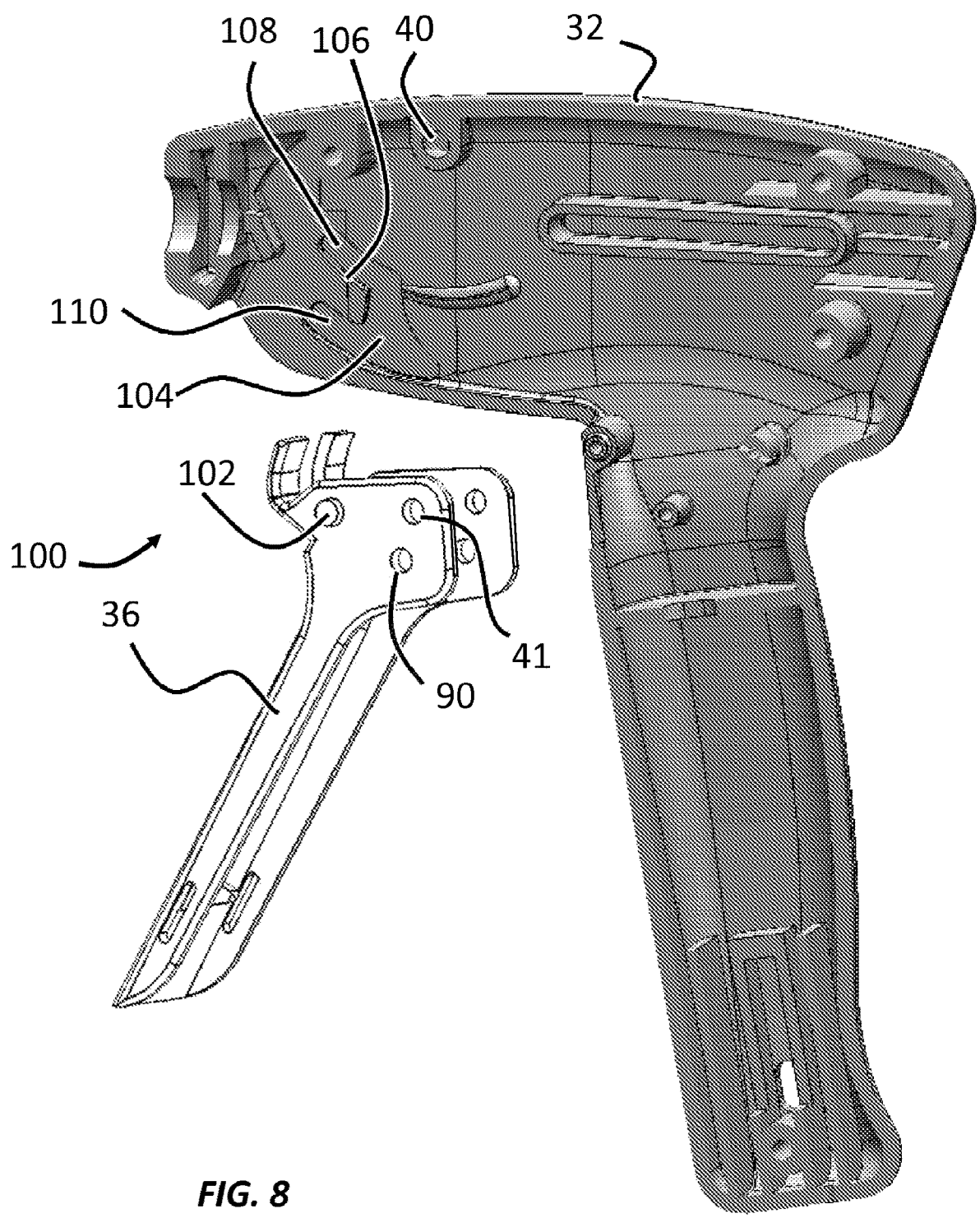
FIG. 8 illustrates an interlock formed between a cam channel, slot, or groove in a handle of the applicator of FIG. 1, shown in cross-section, and a cam follower projecting from a second trigger of the applicator of FIG. 1, shown in a perspective and exploded view orientation according to an embodiment of the present disclosure.

FIG. 8 shows a cross-section of the handle 32 as well as the second trigger 36 exploded therefrom. An interlock 100 is included between the handle 32 and the second trigger 36 to selectively permit and prevent rotational movement of the second trigger 36 with respect to the first trigger 34. The first trigger 34 does not form a part of the interlock 100 in the illustrated embodiment, and therefore is not illustrated in FIG. 8. However, it is to be understood that the first trigger 34 in the embodiment of FIG. 8 would be nevertheless be secured to the second trigger 36 at the pivot 41 as described herein with respect to the other Figures. Additionally, the shaft 12 and the jaw assembly 16 are not illustrated in some Figures, including FIG. 8, but can be included as described herein with respect to the other Figures.

More specifically, the interlock 100 includes a cam follower 102 and a channel 104. In the illustrated embodiment, the cam follower 102 is formed as a protrusion or projection extending from or otherwise coupled to the second trigger 36, and is preferably round in cross section but alternatively may be of other shapes. The cam follower 102 can be integrally formed with the second trigger 36 or affixed thereto as a separate component. The channel 104 may be formed as a groove, depression, notch, slot, or the like in the handle 32. The follower 102 is configured to engage with and/or travel along the channel 104 (and thus will be restricted to movement within the channel 104) when the second trigger 36 is assembled with the handle 32. It is noted that the applicator 10 can include other exemplary embodiments of a single follower 102 and a single channel 104 if desired, but for symmetry, balance, etc., the second trigger 36 may include two cam followers 102 (e.g., another follower 102 hidden from view in FIG. 8 on the opposite lateral side of the second trigger 36 and mirroring the illustrated one of the followers 102 about a plane bisecting the second trigger 36), and the handle 32 may correspondingly include two cam grooves 104 (e.g., another channel 104 located in the half of the handle 32 not shown in FIG. 8, which mirrors the illustrated channel 104 about the plane used to form the cross-sectional view of the handle 32 in FIG. 8).

The mechanical coupling of the follower 102 to the second trigger 36 prevents rotation of the second trigger 36 relative to the first trigger 34 when the follower 102 abuts against the walls or shoulders defining the channel 104. For example, FIGS. 9A-9E show various positions of the follower 102 (without the second trigger 36 for clarity) corresponding to the various combinations of positions of the first and second triggers 34 and 36 of the applicator 10. That is, for example, the position of the follower 102 in FIG. 9A corresponds to an initial, shelf, or delivery configuration of the applicator 10 shown in FIG. 2, i.e., before the triggers 34 or 36 have been actuated.

Figure 9A:
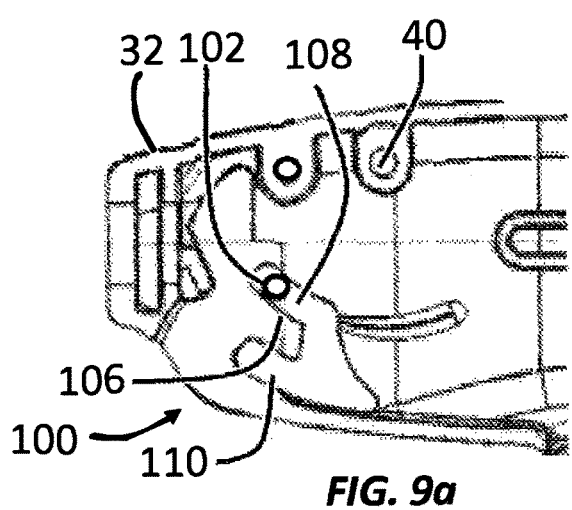
FIGS. 9A-9E illustrate various positions of the cam follower of FIG. 4 along the cam channel of the interlock as first and second triggers of the applicator are moved through the configurations depicted in FIGS. 2-5.
Figure 9B:
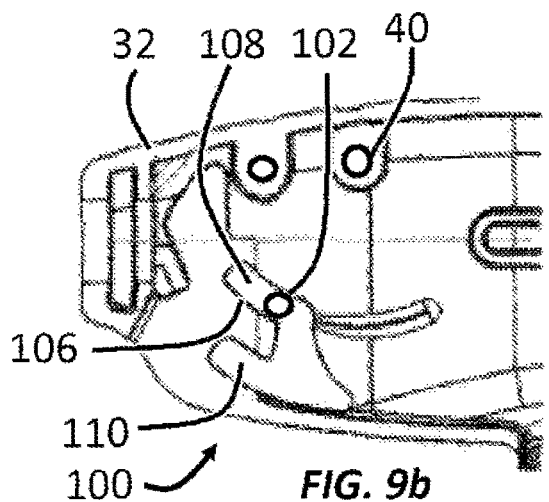

In the position of FIG. 9A, rotation of the second trigger 36 is prevented by interference of the follower 102 with a shoulder 106 of the channel 104. That is, movement of the second trigger 36 relative to the first trigger 34 occurs about the pin 41, which rotationally couples the second trigger 36 to the first trigger 34. Thus, rotation of the second trigger 36 about the pin 41 (if unblocked) would result in the cam follower 102 following an arc defined by a circular path concentric with the pin 41, e.g., illustrated as a circle 107 in FIG. 10. Front FIG. 10, it is clear that rotational movement of the cam follower 102 along an arc defined by the circle 107 is not possible due to interference between the cam follower 102 and the shoulder 106. Accordingly, rotation of the second trigger 36 about the pin 41 relative to the rust trigger 34 is prevented by the interference between the cam follower 102 and the shoulder 106.

The channel 104 is shaped with a leg 108, which permits the second trigger 36 to travel in tandem with the first trigger 34 as the first trigger 34 is moved toward its second position, i.e., rotated about the pivot 40 toward the configuration of the applicator 10 shown in FIG. 3. That is, again referring to FIG. 10, tandem movement of second trigger 36 due to movement of the first trigger 34 would result in the cam follower 102 traveling along an arc defined by a circular path concentric with the pivot 40, illustrated in FIG. 10 by a circle 109. The first leg 108 is arranged to lie substantially along such an arc formed by the circle 109, thereby enabling the cam follower 102 to travel along the leg 108 during rotation of the first anti second triggers 34 and 36 about the pin 40.

FIG. 4B illustrates the position of the follower 102 in the channel 104 when the first trigger 34 is rotated partially toward the configuration of FIG. 3, e.g., with ratcheting tooth surface 62 of the interlock 60 at most only partially driven along and engaged with the pins 64. At the position of FIG. 9B, the shoulder 106 continues to prevent rotation of the second trigger 36 by blocking movement of the follower 104 in the direction necessary to rotate the second trigger 36.

Figure 9C:
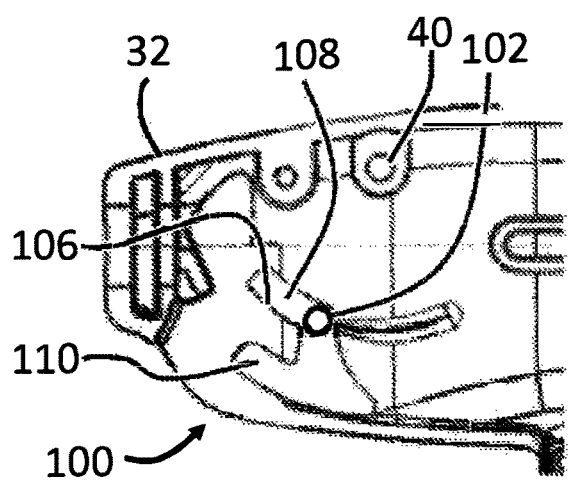

FIG. 9C illustrates the position of the follower 102 after the trigger first 34 has been moved to the configuration of FIG. 3 and the ratcheting tooth surface 62 of the interlock 60 is fully driven along and engaged with the pins 64. It can be appreciated in view of FIGS. 3 and 9C that rotation of the second trigger 36 becomes possible at this position because the shoulder 106 no longer abuts the follower 102. Alternatively stated, it is to be appreciated that tandem movement of the second trigger 36 with the first trigger 34 has shifted the position of the cam follower 102 and the pin 41 relative to the channel 104 (since the pin 41 and the cam follower 102 are directly coupled to the second trigger 36 in the illustrated embodiment). It is to be further understood than this shifting of the position of the pin 41 and the cam follower 102 has also moved the location of the circle 107 to align with a portion 110 of the channel 104 that is transverse to the leg 108 and arranged along an arc that is concentric with respect to the pin 41.

Figure 9D:
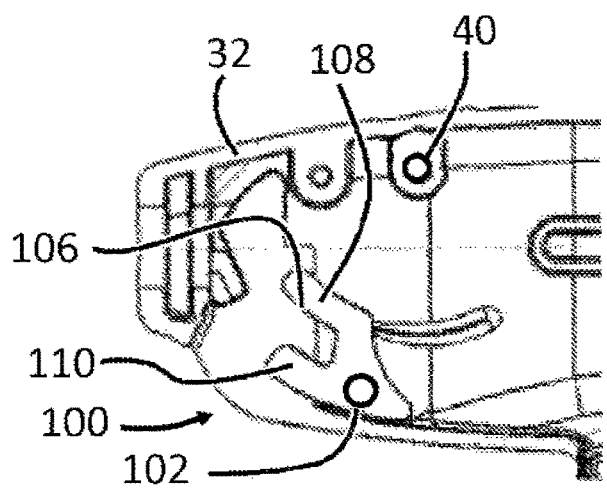

In view of the foregoing it can be seen that the position of the first trigger 34 selectively prevents or permits rotation of the second trigger 36. Again, movement of the first trigger 34 causes tandem movement of the second trigger 36, which results in the follower 102 first traversing along the leg 108 of the channel 104. However, movement of the second trigger 36 relative to the first trigger 34 is prevented due to interference between the cam follower 102 and the shoulder 106. Relative movement of the second trigger 36 with respect to the first trigger 34 is thus prevented until the cam follower 102 is moved to a position at which the cam follower 102 no longer abuts the shoulder 106. FIG. 9D shows the position of the follower 102 after movement of the second trigger 36 relative to the first trigger 34 is permitted and the second trigger 36 has also been actuated to its second position, thereby corresponding to the configuration of the applicator 10 shown in FIG. 4.

Figure 9E:
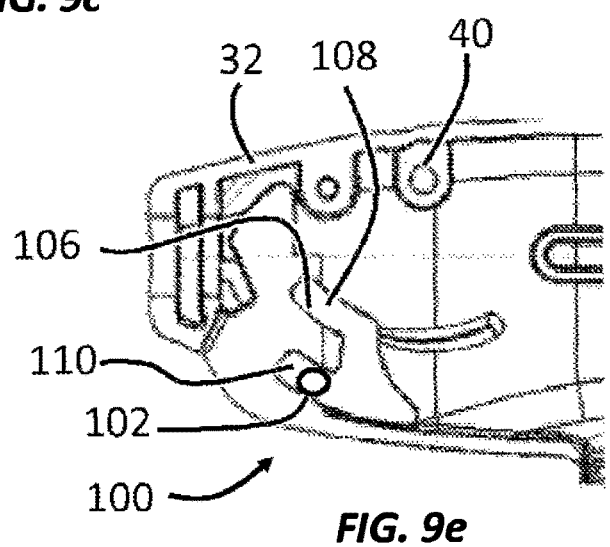

The channel 104 is shaped with another leg 112 that enables the follower 102 to continue to traverse the channel 104 such that the second trigger 36 can again move in tandem with the first trigger 34 as the first trigger 34 is moved to reopen the jaw assembly 16, i.e., as the first trigger 34 is moved back toward its first position. It is to be appreciated that the leg 112, similar to the leg 108, is formed along an arc that is concentric to the pivot 40. This accordingly enables the cam follower 102 to travel along the leg 112 as the second trigger 36 moved in tandem with the first trigger 34 as the first trigger 34 is rotated about the pivot 40. FIG. 9E accordingly shows the corresponding location of the follower 102 in the channel 104 when the first trigger 34 is returned to its first or initial position, which may correspond to the applicator 10 assuming the configuration of FIG. 5 in which the jaw assembly 16 is again opened.

It is to be appreciated that the channel 104 can take other shapes in other embodiments depending on the desired relative movement of the first and second triggers 34 and 36 relative to each other and to the handle 32. More specifically, the channel 104 will include ii leg or portion for each optionally desired stage of movement of the first trigger 34 and of the second trigger 36, with the legs and/or portions of the channel 104 being concentric with respect to the pivot about which rotation is desired for each stage of movement. Thus, in order to sequentially permit (i) tandem movement of both of the first and second hissers 34 and 36 about a first pivot (e.g., the pivot 40), then lip movement of the second trigger 36 relative to the first trigger 34 about a second pivot (e.g., the pivot 41), and then (iii) tandem movement of the first and second triggers 34 and 36 again with respect to the first pivot, the channel 104 will include two legs (e.g., the legs 108 and 112) that are spaced apart hut both concentric with respect to the first pivot (e.g., the pivot 40), which enables the movements of stages (i) and (iii), and a transverse portion (e.g., the portion 110) connecting between the two legs (e.g., the legs 108 and 112) that is formed concentrically with respect to the second pivot (e.g., the pivot 41) to enable the movement of stage (ii).

From the above description and the FIGS. 9A-9E, it is clear that the interlock 100 accordingly prevents rotation of the second trigger 36 until after the trigger first 34 is first rotated, preferably fully rotated (i.e., from a first position to a second position). Since full rotation of the first trigger 34 (e.g., as shown in FIG. 3) corresponds to the closing of the jaw assembly 16, the interlock 100 thus advantageously selectively prevents retraction of the studs 26 (due to rotation of the second trigger 36) until after the jaw assembly 16 is closed. Referring again to the above description, it is again noted that the interlock 60 is released depending on the position of the second trigger 36 relative to the first trigger 34. Thus, the location of the first trigger 34 is first used to release the interlock 100, selectively permitting movement of the second trigger 36 relative to the first trigger 34, and thereafter the location of the second trigger 36 relative to the first trigger 34 is used to release the interlock 60, which selectively permits movement of the first trigger 34 relative to the handle 32 back toward the initial position for the first trigger. In this way, the aforementioned order of the steps of (1) closing the jaws, (2) retracting the studs, and (3) opening the jaws is maintained and ensured by use of either or both of the interlocks 60 and 100.

It is to be appreciated that the interlock 100 can take other forms in non-illustrated embodiments. For example, in one embodiment the channel 104 is alternatively formed with the second trigger 36 and the follower 102 with the handle 32. In another embodiment, part of the channel 104 is formed in one of the handle halves while the other is formed in the other of the handle halves.

Figure 11:
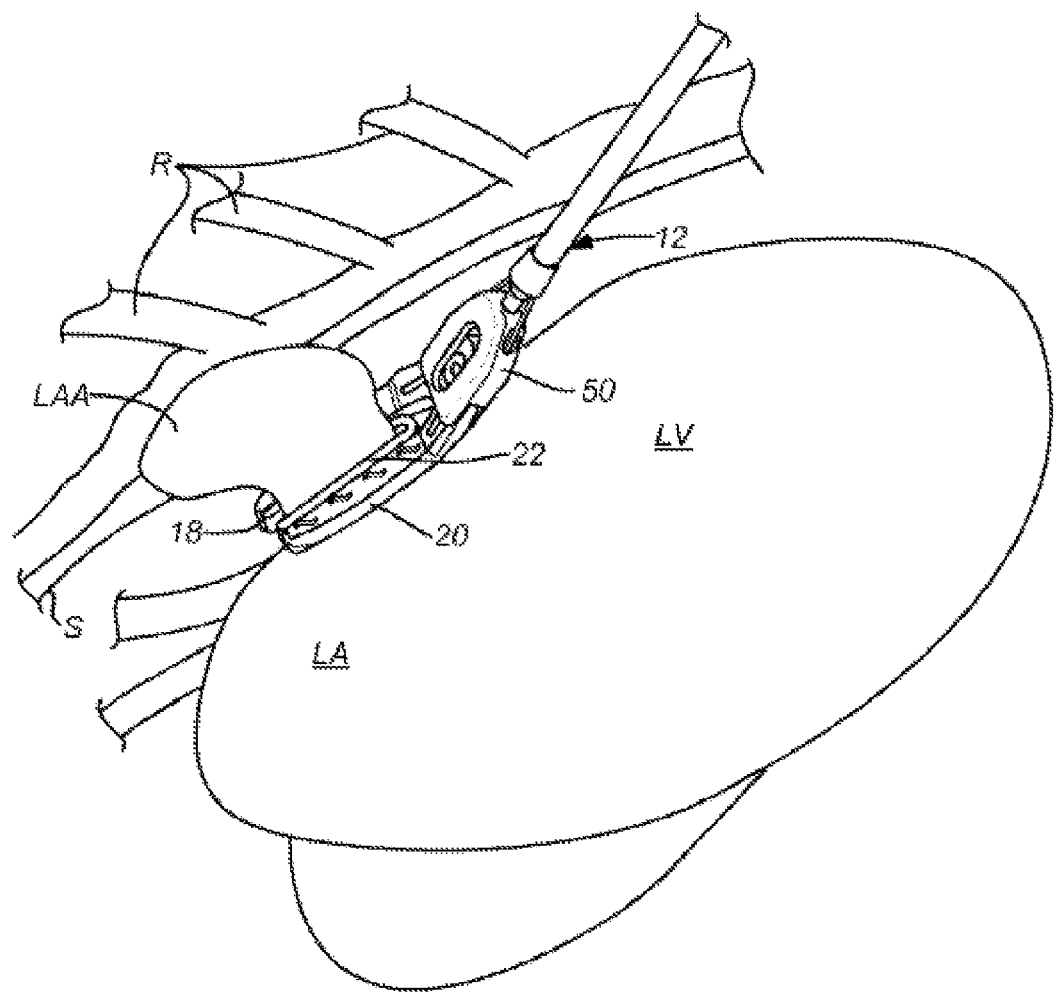
FIG. 11 illustrates use of the applicator according to an example embodiment of the present disclosure, wherein the applicator is used for closing a closure device over a left atrial appendage.

Referring now to FIG. 11, one specific example of use is illustrated. In this example, the fastener applicator 10 is used to deliver one of the fasteners 22 over the base of a left atrial appendage LAA in an open chest, beating heart procedure. The sternum S is opened, spreading the ribs R to provide a working space over the heart. After opening the pericardial sack, the heart may be lifted and turned, for example using a sheet of gauze or other material which is placed behind the heart, to expose the left atrial appendage within the opening as shown in FIG. 10. After the left atrial appendage LAA is exposed, the jaws 18 and 20 of the fastener applicator are placed around the base of the appendage by manipulating the shaft 12, as shown in FIG. 10. The angle of the jaws 18 and 20 relative to the shaft, typically about 15°, is highly advantageous as it allows the jaws to engage the base of the left atrial appendage so that they are generally parallel with the os between the appendage and the left atrium LA. If the plane of the jaws was aliened with the shaft, it would be difficult to achieve this orientation and the risk of closing the appendage and leaving a cul-de-sac (an open space beyond the us and into interior of the left atrial appendage) is greatly increased. Such cul-de-sac is problematic as it can be a source of clotting and, if created, must be closed in the same or later procedure. Once the jaws 18 and 20 properly position the fastener 22 about the base of the left atrial appendage, the jaws are actuated and the fastener deployed as described previously.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, hut that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of operating a fastener applicator, the method comprising:
    repositioning a first trigger of the fastener applicator with respect to a handle from a first position to a second position;
    closing a jaw assembly coupled to the handle of the fastener applicator due to movement of the first trigger to the second position;
    preventing repositioning of a second trigger between an initial position and an actuated position relative to the first trigger by an interlock coupled to the second trigger until the first trigger is moved to the second position, wherein the interlock includes a cam follower engaged with a cam channel, and wherein the handle includes the cam channel and the second trigger includes the cam follower;
    repositioning the second trigger to the actuated position relative to the first trigger after the first trigger is moved to the second position; and
    retracting one or more fastener supporting structures comprising at least one protrusion movably extendable and retractable with respect to at least one jaw of the jaw assembly of the fastener applicator due to repositioning of the second trigger to the actuated position.

2. The method of claim 1 wherein the fastener applicator comprises a second interlock coupled to the first trigger, the method further comprising preventing movement of the first trigger from the second position to the first position with the second interlock until the second trigger is moved to the actuated position relative to the first trigger, and repositioning the first trigger from the second position back to the first position after the second trigger is moved to the actuated position relative to the first trigger.

3. The method of claim 1, wherein rotating the first trigger from the first position to the second position includes traversing the cam follower along a first leg of the channel.

4. The method of claim 3, wherein the first leg is formed concentrically with respect to a pivot about which the first trigger rotates.

5. The method of claim 1, wherein rotating the second trigger to the actuated position relative to the first trigger includes traversing the cam follower along a portion of the channel transverse to the first leg.

6. The method of claim 1, wherein rotating the first trigger from the first position to the second position includes moving the second trigger in tandem with the first trigger.

* * * * *